United States Patent [19]
Godel et al.

[11] Patent Number: 5,385,947
[45] Date of Patent: Jan. 31, 1995

[54] OCTAHYDROPHENANTHRENE DERIVATIVES

[75] Inventors: Thierry Godel, Basel, Switzerland; Eva-Maria Gutknecht, Buggingen-Seefelden, Germany

[73] Assignee: Hoffmann-La Roche Inc., Nutley, N.J.

[21] Appl. No.: 252,131

[22] Filed: May 31, 1994

Related U.S. Application Data

[63] Continuation of Ser. No. 179,215, Jan. 10, 1994, abandoned.

[30] Foreign Application Priority Data

Jan. 15, 1993 [CH] Switzerland .............. 123/93

[51] Int. Cl.$^6$ .................. C07C 211/31; C07C 67/02; A61K 31/21; A61K 31/135
[52] U.S. Cl. ................... 514/654; 514/510; 560/250; 564/379
[58] Field of Search ............ 564/379; 560/250; 514/510, 654

[56] References Cited

U.S. PATENT DOCUMENTS

| | | | |
|---|---|---|---|
| 4,317,910 | 3/1982 | Hauck et al. | 544/154 |
| 5,071,853 | 12/1991 | Bigge et al. | 514/290 |
| 5,180,736 | 1/1993 | Johnson et al. | 514/454 |
| 5,276,053 | 1/1994 | Johnson et al. | 514/437 |

FOREIGN PATENT DOCUMENTS 388977 3/1990 European Pat. Off. .

OTHER PUBLICATIONS

Doyle, et al., Tetrahedron Letters, 23: pp. 1889–1892 (1969).

*Primary Examiner*—Peter O'Sullivan
*Attorney, Agent, or Firm*—George M. Gould; William H. Epstein; Bruce A. Pokras

[57] ABSTRACT

Compounds of the formula:

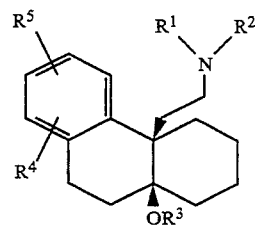

wherein $R^1$ and $R^2$ each individually are hydrogen or lower alkyl optionally substituted by aryl or $C_{3-6}$-cycloalkyl;

$R^4$ and $R^5$ either both are hydrogen or both are halogen or one is hydrogen and the other is halogen, hydroxy, lower alkoxy, aryloxy or amino; and $R^3$ is hydrogen or, where no primary or secondary amino group is present, alkanoyl;

with the proviso that all the groups $R^1$ through $R^5$ cannot simultaneously be hydrogen; as well as pharmaceutically acceptable salts of compounds of formula I with acids have valuable pharmacodynamic properties as non-competitive NMDA antagonists and can accordingly be used as neuroprotectives.

29 Claims, No Drawings

OCTAHYDROPHENANTHRENE DERIVATIVES

This is a continuation of application Ser. No. 08/179,215, filed January 10, 1994, now abandoned.

The present invention is concerned with tricyclic octahydrophenanthrene derivatives, namely compounds of the formula:

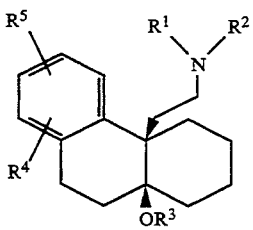

wherein
$R^1$ and $R^2$ each individually are hydrogen or lower alkyl optionally substituted by aryl or $C_{3-6}$-cycloalkyl;
$R^4$ and $R^5$ are both hydrogen or are both halogen or one is hydrogen and the other is halogen, hydroxy, lower alkoxy, aryloxy or amino;
$R^3$ is hydrogen or, where no primary or secondary amino group is present, hydrogen or alkanoyl;
with the proviso that all the groups $R^1$ through $R^5$ cannot simultaneously be hydrogen; as well as pharmaceutically acceptable acid addition salts of compounds of formula I.

The compounds of the invention and rac-cis-4b-(2-amino-ethyl)-4b,5,6,7,8,8a,9,10-octahydrophenanthren-8a-ol (in which the groups $R^1$ through $R^5$ in formula I are simultaneously hydrogen), have valuable pharmacodynamic properties as non-competitive NMDA antagonists and can accordingly be used as neuroprotectives, especially for the treatment or prevention of ischemia, hypoglycaemia, hypoxia, cerebral vasospasms, spasticity, trauma, hemorrhage, infections (viral, bacterial, amoebic, prional), epileptic seizures, autoimmune disorders, withdrawal symptoms, Alzheimer's disease, Parkinson's disease, amyotrophic lateral sclerosis, Huntington's chorea, intoxications, Olivoponto-cerebellar atrophy, spinal injury, schizophrenia, depressions, anxiety states, dependence, pains, autism and mental retardation. Due to their pharmacodynamic property as non-competitive NMDA antagonists, the compounds of the invention and rac-cis-4b-(2-amino-ethyl)-4b,5,6,7,8,8a,9,10-octahydrophenanthren-8a-ol are especially preferred as neuroprotectives to prevent neuronal damage following ischemia or hypoxia in a patient, e.g., after stroke.

Objects of the present invention are the compounds and pharmaceutically acceptable acid addition salts of the invention per se and as therapeutically active substances, medicaments containing such a compound or a salt thereof, and the manufacture of such medicaments. Further objects of the invention are the use of the compounds and salts of the invention, and the use of rac-cis-4b(2-amino-ethyl)-4b,5,6,7,8,8a,9,10-octahydrophenanthren-8a-ol(in which the groups $R^1$ through $R^5$ are simultaneously hydrogen), as neuroprotectives, especially in the treatment or prevention of ischemia, hypoglycaemia, hypoxia, cerebral vasospasms, spasticity, trauma, hemorrhage, infections (viral, bacterial, amoebic, prional), epileptic seizures, autoimmune disorders, withdrawal symptoms, Alzheimer's disease, Parkinson's disease, amyotrophic lateral sclerosis, Huntington's chorea, intoxications, Olivoponto-cerebellar atrophy, spinal injury, schizophrenia, depressions, anxiety states, dependence, pains, autism and mental retardation, the use of the compounds and salts defined earlier for the manufacture of medicaments, as well as a process and intermediates for the manufacture of the novel compounds and salts of the invention.

The term "lower" denotes compounds or groups with a maximum of 7, preferably a maximum of 4, carbon atoms.

The term "alkyl" denotes straight-chain or branched saturated hydrocarbon groups such as methyl, ethyl, propyl and the like.

The term "alkoxy" denotes alkyl groups in the sense of the foregoing definition which are attached via an oxygen atom, such as methoxy and the like.

The term "cycloalkyl" denotes cyclic saturated hydrocarbon groups such as, for example, cyclopropyl or cyclobutyl.

The term "aryl" denotes six-membered, aromatic, optionally substituted cyclic groups attached via a carbon atom, such as, for example, an optionally substituted phenyl group, in which lower alkyl groups can come into consideration as substituents, as well as a heteroaryl group, i.e., for example, a heterocycle which contains one to three nitrogen atoms and which can be unsubstituted or substituted by lower alkyl, nitro, halogen or amino, such as, for example, a pyridyl group.

The term "arylmethoxy" denotes a methoxy group which is substituted by optionally substituted phenyl, such as, for example benzyloxy.

The term "alkanoyl" denotes alkyl groups in the sense of the foregoing definition which are attached via a carbonyl group, and embraces especially lower alkanoyl groups such as acetyl or propionyl and the like.

The term "heteroaryloxy" denotes heteroaryl groups which are attached via an oxygen atom.

The term "arylmethylamino" denotes an amino group which is substituted by methyl and in which the methyl group is, in turn, substituted by aryl, such as, for example, benzylamino.

The term "halogen" signifies fluorine, chlorine, bromine and iodine.

The term "pharmaceutically acceptable acid addition salts" embraces salts with inorganic and organic acids such as hydrochloric acid, hydrobromic acid, nitric acid, sulphuric acid, phosphoric acid, citric acid, formic acid, fumaric acid, maleic acid, acetic acid, succinic acid, tartaric acid, methanesulphonic acid, p-toluenesulphonic acid and the like. Such salts can be manufactured readily by any person skilled in the art having regard to the state of the art and taking into consideration the nature of the compound to be converted into a salt.

Where none of the groups $R^1$ to $R^5$ in formula I has an asymmetric centre, the compounds in accordance with the invention can be present as enantiomers. Otherwise various diastereomers are possible, The invention embraces all possible stereoisomers as well as mixtures thereof, especially racemates.

Preferred compounds of the invention are compounds of the formula:

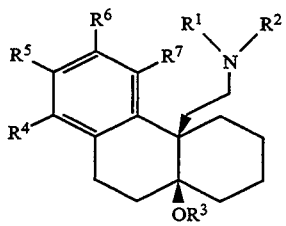

wherein R¹ and R² each independently are hydrogen or lower alkyl optionally substituted by $C_{3-6}$-cycloalkyl, R3 is hydrogen or, where R¹ and R² are both lower alkyl, hydrogen or alkanoyl, and two of the groups $R^4$, $R^5$, $R^6$, and $R^7$ are halogen and the remaining two groups are hydrogen, or three of the groups $R^4$, $R^5$, $R^6$, and $R^7$ are hydrogen and the remaining group is halogen, heteroaryloxy, lower alkoxy or hydroxy.

Particularly preferred are compounds of formula I' in which R¹ and R² each are both hydrogen or are both lower alkyl, $R^3$ is hydrogen or, where R¹ and R² are both lower alkyl, hydrogen or alkanoyl, and two of the groups $R^4$, $R^5$, $R^6$, and $R^7$ are halogen and the remaining two groups are hydrogen, or three of the groups $R^4$, $R^5$, $R^6$, and $R^7$ are hydrogen and the remaining group is halogen, lower alkoxy or hydroxy.

Especially preferred are compounds of formula I' in which R¹ and R² are lower alkyl, preferably methyl, $R^3$ is hydrogen or alkanoyl wherein the alkanoyl is preferably acetyl, and all of the groups $R^4$, $R^5$, $R^6$ and $R^7$ are hydrogen, or three of the groups $R^4$, $R^5$, $R^6$ and $R^7$ are hydrogen and the remaining group is halogen or hydroxy. It is very especially preferred that the groups $R^4$, $R^5$, and $R^7$ are hydrogen and $R^6$ is halogen or hydroxy.

Also especially preferred are compounds of formula I' in which R¹, R² and $R^3$ are all hydrogen, and three of the groups $R^4$, $R^5$, $R^6$ and $R^7$ are hydrogen and the remaining group is halogen or hydroxy. It is very especially preferred that the groups $R^4$, $R^5$, and $R^7$ are hydrogen and the group $R^6$ is halogen or hydroxy.

Especially preferred compounds of formula I' are:
rac-cis-4b-(2-dimethylamino-ethyl)-4b,5,6,7,8,8a,9,10-octahydrophenanthren-8a-ol;
rac-cis-3-chloro-4b-(2-dimethylamino-ethyl)-4b,5,6,7,8,8a,9,10-octahydro-phenanthren-8a-ol;
(−)-cis-3-chloro-4b-(2-dimethylamino-ethyl)-4b,5,6,7,8,8a,9,10-octahydrophenanthrene-8a-ol;
(+)-cis-3-chloro-4b-(2-dimethylamino-ethyl)-4b,5,6,7,8,8a,9,10-octahydrophenanthren-8a-ol; and
rac-cis-4b-(2-dimethylamino-ethyl)-4b,5,6,7,8,8a,9,10-octahydro-phenanthrene-3,8a-diol.

Other preferred compounds of formula I' are:
rac-cis-4b-(2-amino-ethyl)-3-fluoro-4b,5,6,7,8,8a,9,10-octahydro-phenanthren-8a-ol;
rac-cis-4b-(2-amino-ethyl)-3-chloro-4b,5,6,7,8,8a,9,10-octahydro-phenanthren-8a-ol;
rac-cis-4b-(2-amino-ethyl)-3-bromo-4b,5,6,7,8,8a,9,10-octahydro-phenanthren-8a-ol;
rac-cis-4b-(2-amino-ethyl)-4b,5,6,7,8,8a,9,10-octahydro-phenanthrene-3,8a-diol;
(+)-cis-4b-(2-amino-ethyl)-4b,5,6,7,8,8a,9,10-octahydro-phenanthrene-3,8a-diol;
(−)-cis-4b-(2-amino-ethyl)-4b,5,6,7,8,8a,9,10-octahydro-phenanthrene-3,8a-diol;
rac-cis-4b-(2-dimethylamino-ethyl)-3-fluoro-4b,5,6,7,8,8a,9,10-octahydro-phenanthren-8a-ol;
rac-cis-4b-(2-dimethylamino-ethyl)-3-methoxy-4b,5,6,7,8,8a,9,10-octahydro-phenanthren-8a-ol;
acetic acid rac-cis-4b-(2-dimethylamino-ethyl)-3-fluoro-4b,5,6,7,8,8a,9,10-octahydro-phenanthren-8a-yl ester;
acetic acid rac-cis-3-chloro-4b-(2-dimethylamino-ethyl)4b,5,6,7,8,8a,9,10-octahydro-phenanthren-8-a-yl ester; and
rac-cis-4b-(2-amino-ethyl)-3-chloro-1-fluoro-4b,5,6,7,8,8a,9,10-octahydro-phenanthren-8a-ol.

The novel octahydrophenanthrene derivatives of the invention and their salts can be manufactured in accordance with the invention by:

a) for the manufacture of a compound of the invention in which R¹, R² and $R^3$ each are hydrogen and $R^4$ and $R^5$ both are halogen or one is hydrogen and the other is halogen, lower alkoxy or aryloxy, reducing a compound of the formula:

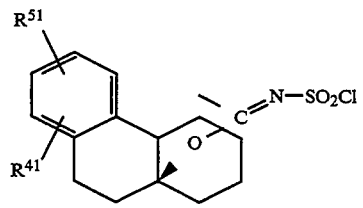

wherein $R^{41}$ and $R^{51}$ both are halogen or one is hydrogen and the other is halogen, lower alkoxy or aryloxy, or b) for the manufacture of a compound of the invention in which one of R¹ and R² is hydrogen and the other is lower alkyl optionally substituted by aryl or $C_{3-6}$-cycloalkyl or R¹ and R² each are lower alkyl optionally substituted by aryl or $C_{3-6}$-cycloalkyl, $R^3$ is hydrogen and $R^4$ and $R^5$ both are hydrogen or halogen or one is hydrogen and the other is halogen, lower alkoxy or aryloxy, correspondingly mono- or disubstituting a compound of the formula:

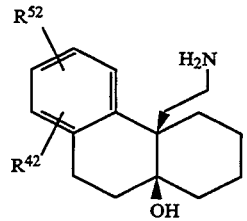

wherein $R^{42}$ and $R^{52}$ both are hydrogen or halogen or one is hydrogen and the other is halogen, lower alkoxy or aryloxy, at the primary amino group; or c) for the manufacture of a compound of the invention in which R¹ and R² are lower alkyl optionally substituted by aryl or $C_{3-6}$cycloalkyl, $R^3$ is alkanoyl and $R^4$ and $R^5$ both are hydrogen or halogen or one is hydrogen and the other is halogen, lower alkoxy or aryloxy, treating a compound of the formula:

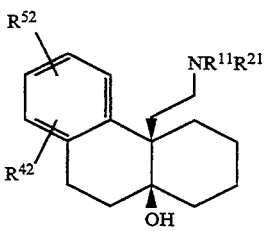

wherein $R^{11}$ and $R^{21}$ are lower alkyl optionally substituted by aryl or $C_{3-6}$-cycloalkyl and $R^{42}$ and $R^{52}$ are as defined above, with a compound yielding an alkanoyl group, or d) for the manufacture of a compound of the invention in which one of $R^4$ and $R^5$ is hydrogen and the other is hydroxy, hydrogenating a compound of the formula:

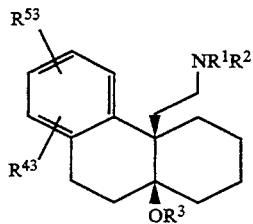

wherein $R^1$, $R^2$ and $R^3$ are as defined above and one of $R^{43}$ and $R^{53}$ is hydrogen and the other is arylmethoxy, in the presence of a catalyst, or e) for the manufacture of a compound of the invention in which $R^1$ and $R^2$ have the above significance, $R^3$ is hydrogen and one of $R^4$ and $R^5$ is hydrogen and the other is amino, hydrogenating a compound of the formula:

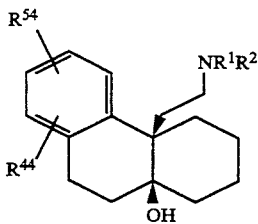

wherein $R^1$ and $R^2$ are as defined above and one of $R^{44}$ and $R^{54}$ is hydrogen and the other is arylmethylamino, in the presence of a catalyst, or f) for the manufacture of a compound of the invention in which $R^1$, $R^2$ and $R^3$ are as defined above and one of $R^4$ and $R^5$ is hydrogen and the other is heteroaryloxy, treating a compound of the formula:

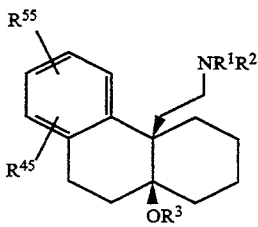

wherein $R^1$, $R^2$ and $R^3$ are as defined above and one of $R^{45}$ and
$R^{55}$ is hydrogen and the other is hydroxy, with a compound of the formula X-Z, wherein Z a leaving group and X is heteroaryl, g) if desired, separating a diastereomeric mixture obtained and/or resolving a racemate obtained, and/or h) if desired, converting a compound of the invention obtained into a pharmaceutically acceptable salt.

Compounds of the invention in which $R^1$, $R^2$ and $R^3$ are hydrogen and $R^4$ and $R^5$ both are halogen or one is hydrogen and the other is halogen, lower alkoxy or aryloxy can be manufactured in accordance with process variant a). This is effected by reducing a compound of formula II in which $R^{41}$ and $R^{51}$ both are halogen or one is hydrogen and the other is halogen, lower alkoxy or aryloxy, for example with lithium aluminium hydride or lithium borohydride or similar reducing agents in the presence of an inert solvent such as, for example, dioxan or THF or similar inert solvents, and subsequently reacting with aqueous alkali hydroxide solution such as, for example, NaOH solution. The reduction is preferably carried out in a temperature range of room temperature to the reflux temperature of the reaction mixture, conveniently at the reflux temperature.

Compounds of the invention in which one of $R^1$ and $R^2$ is hydrogen and the other is lower alkyl optionally substituted by aryl or $C_{3-6}$-cycloalkyl or $R^1$ and $R^2$ each are lower alkyl optionally substituted by aryl or $C_{3-6}$-cycloalkyl, $R^3$ is hydrogen and $R^4$ and $R^5$ both are hydrogen or halogen or one is hydrogen and the other is halogen, lower alkoxy or aryloxy can be manufactured in accordance with process variant b).

This can be accomplished by correspondingly mono- or disubstituting a compound of formula la in which $R^{42}$ and $R^{52}$ both are hydrogen or halogen or one is hydrogen and the other is halogen, lower alkoxy or aryloxy at the primary amino group. This can be effected, e.g., by acylating the compounds of formula la with a compound which yields an alkanoyl group optionally substituted by aryl or $C_{3-6}$-cycloalkyl or a formyl group or an aryl group attached via a carbonyl group or a $C_{3-6}$-cycloalkyl group attached via a carbonyl group and subsequently reducing the product, whereupon the thus-obtained compound is optionally again acylated with a compound which yields an alkanoyl group optionally substituted by aryl or $C_{3-6}$-cycloalkyl or a formyl group or an aryl group attached via a carbonyl group or a $C_{3-6}$-cycloalkyl group attached via a carbonyl group, and the product is subsequently reduced. The hydroxy group present in the compound of formula la is simultaneously acylated, but is liberated in the subsequent reduction.

The reactive derivatives of the corresponding carboxylic acids, for example carboxylic acid chlorides, which are preferably prepared using thionyl chloride in the presence of a small amount of N,N-dimethylformamide in toluene, are particularly suitable for the acylation. The acylation is effected in the presence of a base. Suitable bases are, for example, amines such as triethylamine, pyridine and the like. The reaction is preferably carried out in a temperature range of about room temperature to the reflux temperature of the reaction mixture, especially at room temperature.

The formyl group can be introduced, for example, by reacting a compound of formula la with a mixture of ethyl formate and formic acid; this mixture simultaneously serves as the solvent. The reaction is preferably carried out at the reflux temperature of the reaction mixture.

Lithium aluminium hydride is, for example, a suitable reducing agent. The reduction is carried out in inert organic solvents, for example THF or similar solvents. The reaction temperature preferably lies in a temperature range of room temperature to the reflux temperature, especially at the reflux temperature of the reaction mixture.

A compound of formula Ia can also be dimethylated in one step, for example by treatment with a mixture of aqueous formic acid solution and aqueous formaldehyde solution; this mixture simultaneously serves as the solvent. The reaction is preferably carried out at the reflux temperature of the reaction mixture.

Compounds of the invention in which $R^1$ and $R^2$ are lower alkyl optionally substituted by aryl or $C_{3-6}$-cycloalkyl, $R^3$ is alkanoyl and $R^4$ and $R^5$ both are hydrogen or halogen or one is hydrogen and the other is halogen, lower alkoxy or aryloxy can be manufactured in accordance with process variant c). This can be accomplished by, for example, reacting a reactive derivative of a corresponding carboxylic acid, prepared in a manner known per se, with a compound of formula Ib in which $R^{11}$ and $R^{21}$ are lower alkyl optionally substituted by aryl or $C_{3-6}$-cycloalkyl and $R^{42}$ and $R^{52}$ are as defined above. Reactive carboxylic acid derivatives which are used are, for example, the corresponding carboxylic acid chlorides which are prepared from the corresponding carboxylic acids, conveniently using thionyl chloride in the presence of a small amount of N,N-dimethylformamide in toluene. The corresponding imidazolides can also be prepared by treating the carboxylic acid with 1,1'-carbonyl-diimidazole in an inert solvent such as, for example, N,N-dimethylformamide. The reaction of the reactive carboxylic acid derivative with a compound of formula Ib is effected in the presence of a base. Suitable bases are, for example, amines such as triethylamine, pyridine and the like. The reaction is preferably carried out in a temperature range of about room temperature to the reflux temperature of the reaction mixture, especially at room temperature.

Compounds of the invention in which $R^1$, $R^2$ and $R^3$ are as defined above and one of $R^4$ and $R^5$ is hydrogen and the other is hydroxy can be manufactured in accordance with process variant d).

In this reaction, a compound of formula III in which $R^1$, $R^2$ and $R^3$ are as defined above and one of $R^{43}$ and $R^{53}$ is hydrogen and the other is arylmethoxy is hydrogenated in the presence of a catalyst such as, for example, a palladium catalyst. Lower alcohols such as, for example, methanol or ethanol, are particularly suitable solvents. The reaction is preferably carried out at room temperature.

Compounds of the invention in which $R^1$ and $R^2$ are as defined above, $R^3$ is hydrogen and one of $R^4$ and $R^5$ is hydrogen and the other is amino can be manufactured in accordance with process variant e). Thus, a compound of formula IV in which $R^1$ and $R^2$ have the above significance and one of $R^{44}$ and $R^{54}$ is hydrogen and the other is arylmethylamino is hydrogenated in the presence of a catalyst, for example a palladium catalyst. Lower alcohols such as, for example, methanol or ethanol are particularly suitable solvents. The reaction is preferably carried out at room temperature and a pressure of about 50 bar.

Compounds of formula I in which $R^1$, $R^2$ and $R^3$ are as defined above and one of $R^4$ and $R^5$ is hydrogen and the other is heteroaryloxy can be manufactured in accordance with process variant f). This process variant is preferably carried out by treating a compound of formula Ic in which $R^1$, $R^2$ and $R^3$ are as defined above and one of $R^{45}$ and $R^{55}$ is hydrogen and the other is hydroxy with a reactive heteroaryl derivative, for example a heteroaryl halide such as 2-bromopyridine or the like. Suitable solvents are, for example, pyridine or similar solvents which are inert under the reaction conditions. The reaction is preferably carried out at the reflux temperature of the reaction mixture.

The separation of diastereomeric mixtures and/or the resolution of racemates in accordance with process variant g) can be effected according to generally conventional methods, whereby it can be convenient to carry this out not only on compounds of formula I, but already at an earlier stage of the synthesis, e.g. at the stage of the compounds of formula III or IV.

Compounds of the invention can be converted into pharmaceutically acceptable acid addition salts in accordance with process is variant h). These salts can be not only salts with inorganic acids, but also salts with organic acids. Hydrochlorides, hydrobromides, nitrates, sulphates, phosphates, citrates, formates, fumarates, maleates, acetates, succinates, tartrates, methansulphonates, p-toluenesulphonates and the like are examples of such salts. These salts can be manufactured according to methods which are known per se and familiar to any person skilled in the art.

The compounds of formula II which are used as starting materials can be prepared, for example, in accordance with the following Reaction Scheme and the subsequent explanation of the various reactions.

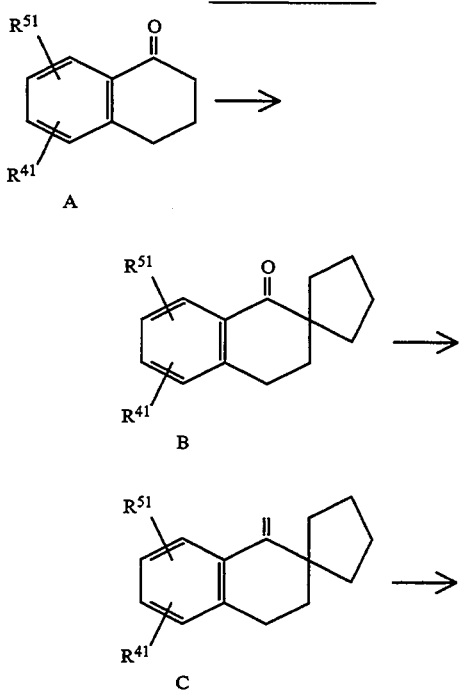

Reaction Scheme I

-continued
Reaction Scheme I

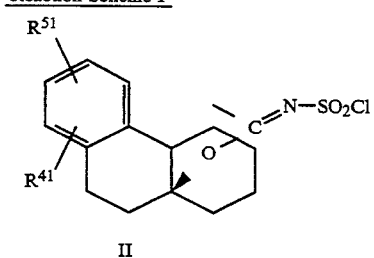

II $R^{41}$ and $R^{51}$ both are halogen or one is hydrogen and the other is halogen, lower alkoxy or aryloxy.

The tetralones of general formula A are known or can be prepared analogously to known synthetic routes. Novel tetralones have been prepared as follows:

1) 8-Chloro-1,2,3,4-tetrahydro-naphthalen-1-one:
   a) Orthometallation of 1,2,3,4-tetrahydronaphthalen-1-ol with butyllithium and N,N,N',N'-tetramethylenediamine (TMEDA) in hexane according the method described in Synthesis 1981, 59;
   b) quenching with hexachloroethane according to V. Snieckus, Chem. Rev. 1990, 90, 879;
   c) Jones oxidation.

2) 7-Chloro-5-fluoro-1,2,3,4-tetrahydro-naphthalen-1-one:
   a) Bromination of 4-chloro-2-fluorotoluene with N-bromosuccinimide in carbon tetrachloride in the presence of catalytic amounts of dibenzoyl peroxide;
   b) oxidation to the aldehyde according to the method described in Tetr. Letters 1990, 31, 4825;
   c) Wittig reaction with 2-(1,3-dioxan-2-yl)-ethyl-triphenylphosphonium bromide and potassium tertbutylate in DMSO/THF;
   d) hydrogenation of the alkene with Pd—C catalyst (10%) in THF at RT under normal pressure;
   e) ketal cleavage to the aldehyde with Cr(III) chloride in 4N aqueous hydrochloric acid according to the method described in synthesis, 1979, 132;
   f) oxidation with potassium permanganate and sodium dihydrogen phosphate in tert-butanol according to the method described in Tetr. Letters 1986, 27, 4537;
   g) cyclization with polyphosphoric acid at about 100° C.

3) 5,7-Dichloro-1,2,3,4-tetrahydro-naphthalen-1-one:
   a) Wittig reaction of 2,4-dichlorobenzaldehyde with 2-(1,3-dioxan-2-yl) -ethyl-triphenyl-phosphonium bromide and potassium tert-butylate in DMSO/THF;
   b) hydrogenation of the alkene with Pd—C catalyst (10%) in THF at room temperature under normal pressure;
   c) ketal cleavage to the aldehyde with Cr(III) chloride in 4N aqueous hydrochloric acid according to the method described in Synthesis, 1979, 132;
   d) oxidation with potassium permanganate and sodium dihydrogen phosphate in tert-butanol according to the method described in Tetr. Letters 1986, 27, 4537;
   f) cyclization with polyphosphoric acid at about 100° C.

The compound corresponding to formula II in which $R^{41}$ and $R^{51}$ each is hydrogen is known, see Tetr. Letters 1969, 1889. Compounds of formula II in which $R^{41}$ and $R^{51}$ are as defined above can be prepared analogously thereto:

A compound of formula B is obtained by reacting a tetralone of formula A with a base such as, for example, potassium tert-butanolate in a suitable organic solvent, preferably THF, and subsequent reaction with 1,4-dibromobutane. This reaction is preferably effected under a protective gas atmosphere at low temperatures, preferably in a temperature range of about −50° C. about −80° C.

The compounds of formula B are treated with (triphenylphosphonio)-methanide compounds of formula C. (Triphenylphosphonio)methanide is preferably generated in situ from a methyltriphenylphosphonium halide/alkali amide mixture in an inert solvent such as, for example, THF at room temperature.

The desired compound of formula II is obtained by reacting a compound of formula C, with chlorosulphonyl isocyanate in a suitable solvent, for example an ether, under a protective gas atmosphere and at low temperature, preferably at about −50° C. to about −80° C.

An analogous procedure is followed for the preparation of compounds of formula III, but starting from analogues of compounds of formula A in which one of $R^{41}$ and $R^{51}$ is hydrogen and the other is arylmethoxy; the subsequent procedure being analogous to process variant a) and optionally b) and if necessary c).

The synthesis of a compound of formula IV starts, in contrast to the methods described above, according to the following Scheme:

Reaction Scheme II

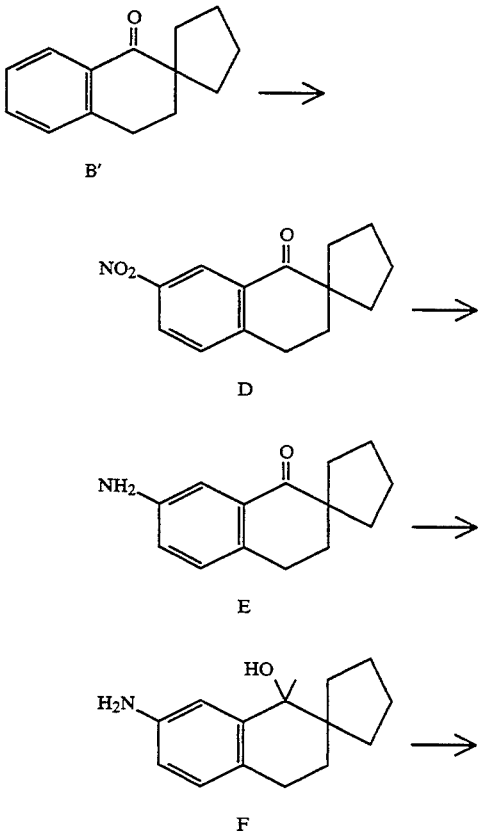

-continued
Reaction Scheme II

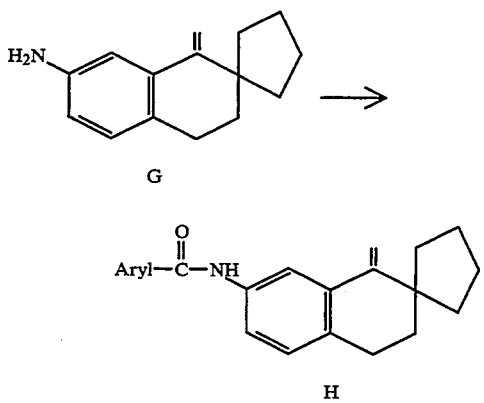

a) Firstly, a compound of formula B' is treated with a nitrating agent, for example with a sulphuric acid/nitric acid mixture. Sulphuric acid is conveniently used as the solvent and the reaction is preferably effected at the reflux temperature of the reaction mixture.

b) The thus-obtained nitro-spiro compound of formula D is hydrogenated in an inert solvent such as, for example, THF at the reflux temperature of the reaction mixture in the presence of a suitable catalyst, for example a Pd/C catalyst.

c) The amino compound of formula E is treated in an inert solvent, preferably an ether, with methyllithium. The reaction is preferably carried out at reflux temperature.

d) The compound of formula F is dehydrated to the corresponding methylene compound of formula G with suitable agents, for example, with iodine.

e) By reacting the compound of formula G with an arylcarboxylic acid derivative, for example benzoyl chloride, in the presence of a base such as, for example, triethylamine in an inert solvent such as THF or similar solvents there is obtained a compound of formula H. The corresponding compound IV is obtained by reaction with chlorosulphonyl isocyanate and subsequent reduction with lithium aluminium hydride, whereupon, if desired, the procedure analogous to process variant b) is followed.

The compounds of formula II used as intermediates are novel and are also an object of the present invention, and the same is true for analogues of compounds of formula II in which one of $R^{41}$ and $R^{51}$ is hydrogen and the other is arylmethoxy or arylcarbonylamino. Furthermore, the intermediates of formulae III and IV are also novel and are likewise objects of the present invention.

As mentioned earlier, the compounds of the invention as well as rac-cis-4b-(2-amino-ethyl)-4b,5,6,7,8,8a,9,10-octahydro-phenanthren-8a-ol have a pharmacological activity as non-competitive NMDA antagonists. Having regard to this activity, the compounds of the invention or rac-cis-4b-(2-amino-ethyl)-4b,5,6,7,8,8a,9,10-octahydro-phenanthren-8a-ol and their pharmaceutically acceptable acid addition salts can be used as neuroprotectives, especially for the treatment or prevention of ischemia, hypoglycaemia, hypoxia, cerebral vasospasms, spasticity, trauma, hemorrhage, infections (viral, bacterial, amoebic, prional), epileptic seizures, autoimmune disorders, withdrawal symptoms, Alzheimer's disease, Parkinson's disease, amyotrophic lateral sclerosis, Huntington's chorea, intoxications, Olivopontocerebellar atrophy, spinal injury, schizophrenia, depressions, anxiety states, dependence, pains, autism and mental retardation. Due to their pharmacodynamic property as NMDA antagonists, the compounds of the invention and rac-cis-4b-(2-amino-ethyl)-4b,5,6,7,8,8a,9,10-octahydro-phenanthren-8a-ol and their pharmaceutically acceptable acid addition salts are especially preferred as neuroprotectives to prevent neuronal damage following ischemia or hypoxia in a patient, e.g., after stroke.

The pharmacological activity of some compounds in accordance with the invention and of rac-cis-4b-(2-amino-ethyl)4b,5,6,7,8,8a,9,10-octahydro-phenanthren-8a-ol was determined in vitro according to the method described in *Europ. J. Pharmacol.* 135, 261 (1987). According to this method [namely the 3H-MK801 (dizocilpine) binding test] the inhibition of the binding of dizocilpine to the specific binding sites in rat cortex by the respective test substances is determined. The $IC_{50}$ ("50% inhibiting concentration") is that concentration of the respective test substance which brings about a 50 percent inhibition of the specific binding of dizocilpine to the specific binding sites in the rat cortex.

The thus-determined activity of some compounds in accordance with the invention will be evident from the $IC_{50}$ values set forth in the following Table; moreover, the Table contains data concerning their toxicity (lowest lethal dosage=LLD in the mouse, p.o.).

| Test substance | [3H]-MK801 binding, $IC_{50}$ [nM/l] | Toxicity LLD (mg/kg) |
|---|---|---|
| rac-cis-4b-(2-Amino-ethyl)-3-chloro-4b,5,6,7,8,8a,9,10-octahydro-phenanthren-8a-ol hydrochloride | 84.7 | 500 |
| rac-cis-4b-(2-Amino-ethyl)-3-chloro-1-fluoro-4b,5,6,7,8,8a,9,10-octahydro-phenanthren-8a-ol hydrochloride | 107 | 1000 |
| rac-cis-4b-(2-Amino-ethyl)-4b,5,6,7,8,8a,9,10-octahydro-phenanthrene-3,8a-diol hydrochloride | 73.4 | 1000 |
| rac-cis-4b-(2-Dimethylamino-ethyl)-4b,5,6,7,8,8a,9,10-octahydro-phenanthren-8a-ol hydrochloride | 453 | — |
| (-)-cis-3-Chloro-4b-(2-dimethylamino-ethyl)-4b,5,6,7,8,8a,9,10-octahydro-phenanthren-8a-ol hydrochloride | 254 | 375 |
| rac-cis-4b-(2-Amino-ethyl)-4b,5,6,7,8,8a,9,10-octahydro-phenanthren-8a-ol hydrochloride | 93 | 250 |

The compounds of the invention as well as rac-cis-4b-(2-amino-ethyl)-4b,5,6,7,8,8a,9,10-octahydro-phenanthren-8a-ol and their pharmaceutically usable salts can be used as medicaments, e.g., in the form of pharmaceutical preparations (compositions). The pharmaceutical preparations can be administered enterally such as orally, e.g., in the form of tablets, coated tablets, dragées, hard and soft gelatine capsules, solutions, emulsions or suspensions, nasally, e.g., in the form of nasal sprays, or rectally, e.g., in the form of suppositories. The administration can also be effected parenterally such as subcutaneously, intramuscularly or intravenously, e.g., in the form of injection solutions.

For the manufacture of tablets, coated tablets, dragées and hard gelatine capsules the compounds as well as their pharmaceutically usable salts can be processed with pharmaceutically acceptable, inorganic or organic excipients. Lactose, maize starch or derivatives thereof, talc, stearic acid or its salts, etc. can be used e.g. as such excipients for tablets, dragées and hard gelatine capsules. Suitable excipients for soft gelatine capsules are, e.g., vegetable oils, waxes, fats, semi-solid and liquid polyols, etc. Suitable excipients for the manufacture of solutions and syrups are, e.g., water, polyols, saccharose, invert sugar, glucose etc. Suitable excipients for injection solutions are, e.g., water, alcohols, polyols, glycerol, vegetable oils, etc. Suitable excipients for suppositories are, e.g., natural or hardened oils, waxes, fats, semi-liquid or liquid polyols, etc. Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, coating agents or antioxidants. They can also contain other therapeutically valuable substances.

In accordance with the invention, compounds of of the invention as well as rac-cis-4b-(2-amino-ethyl)-4b,5,6,7,8,8a,9, 10-octahydro-phenanthren-8a-ol and their pharmaceutically acceptable acid addition salts can be used as neuroprotectives, especially in the treatment or prevention of ischemia, hypoglycaemia, hypoxia, cerebral vasospasms, spasticity, trauma, hemorrhage, infections (viral, bacterial, amoebic, prional), epileptic seizures, autoimmune disorders, withdrawal symptoms, Alzheimer's disease, Parkinson's disease, amyotrophic lateral sclerosis, Huntington's chorea, intoxications, Olivoponto-cerebellar atrophy, spinal injury, schizophrenia, depressions, anxiety states, dependence, pains, autism and mental retardation. Due to their pharmacodynamic property as NMDA antagonists, the compounds of the invention are especially preferred as neuroprotectives to prevent neuronal damage following ischemia or hypoxia in a patient, e.g., after stroke.

The dosage can vary within wide limits and will, of course, be fitted to the individual requirements in each particular case. In the case of oral administration, the daily dosage lies in a range of about 50-500 mg, although the upper limit can also be exceeded should this be found to be indicated.

The following Examples serve to illustrate the present invention in more detail. However, they are not intended to limit its scope in any manner. All temperatures are given in degrees Celsius ("RT"=room temperature).

EXAMPLE 1

1.1. 43.7 g of potassium tert-butylate (0.39 mol) were added portionwise at $-78°$ C. to a solution of 32.0 g of 7-fluoro-1,2,3,4-tetrahydro-naphthalen-1-one (0.19 mol) in 320 ml of THF while gassing with argon. The mixture was stirred at $-78°$ C. for 2 hrs. and then a solution of 40 ml of 1,4-dibromobutane (73 g, 0.338 mol) in 40 ml of THF was added dropwise. The cooling bath was removed and the mixture was stirred at RT for 16 hrs. Water was added, the mixture was extracted with ether, the organic phase was washed with a saturated aqueous sodium chloride solution, dried over $MgSO_4$, filtered, concentrated and the residue was chromatographed over silica gel with toluene. The product was distilled through a 20 cm Vigreux column. Yield: 29.4 g (76%) of 7'-fluoro-3'4'-dihydro-spiro[cyclopentan-1,2'(1'H)-naphthalen]-1'-one as a colourless liquid; b.p. 98°–102° C./0. 11 Torr.

1.2. 123 g of methyltriphenylphosphonium bromide/sodium amide mixture (0.29 mol) were stirred for 3/4 hr. in 500 ml of THF at RT under argon. A solution of 29.4 g of 7'-fluoro-3'4'-dihydro-spiro[cyclopentan-1,2'(1'H)-naphthalen]-1'-one (0.13mol)in 50 ml of THF was added dropwise to the yellow suspension and the mixture was then stirred for 18 hrs. Water was added, the mixture was extracted with ether, the organic phase was washed with a saturated aqueous sodium chloride solution, dried over $MgSO_4$, filtered off, concentrated and the residue was chromatographed over silica gel with toluene. Yield: 26.3 g (90%) of 7'-fluoro-1'-methylene-3'4'-dihydro-spiro[cyclopentane-1,2'(1'H)-naphthalene] as a colourless liquid.

MS: m/e (% basic peak)=216 ($C_{15}H_{17}F^{30}$, 20), 175 (100), 159 (24), 147 (16), 133 (15), 109(4).

1.3. A solution of 12.9 ml of chlorosulphonyl isocyanate (0.15 mol) in 40 ml of ether was added dropwise at-78° C. while gassing with argon to a solution of 26.3 g of 7'-fluoro-1'-methylene -3'4'-dihydro-spiro[cyclopentane-1,2'(1'H)-naphthalene] (0.12 mol) in 250 ml of ether. The mixture was stirred at $-78°$ C. for 15 min, left to warm to RT and stirred for a further 15 hrs. The resulting crystallizate was filtered off under suction, washed with ether and dried in a vacuum. Yield: 27.1 g (62%) of rac-cis-8-fluoro- 1,2,4,5-tetrahydro-3a,9b-butano-naphtho[2,1 -b]furan-2-ylidene-sulphamoyl chloride [(E) or (Z) or (E/Z) mixture] as yellowish crystals; m.p. 161°–162° C.

1.4. 14.4 g (0.38 mol) of lithium aluminium hydride were suspended in 300 ml of dioxan under argon. A solution of 27.1 g of 8-fluoro-1,2,4,5-tetrahydro-3a, 9b-butano-naphtho[2,1 -b] furan-2-ylidene-sulphamoyl chloride [(E) or (Z) or (E/Z) mixture] (0.076 mol) in 300 ml of THF was added dropwise and the mixture was boiled under reflux for 17 hrs. 15 ml of water, 15 ml of a 15 percent aqueous NaOH solution and 45 ml of water were cautiously added dropwise in succession at RT to form a complete white precipitate. After filtration and concentration the residue was chromatographed over silica gel with methanol/ammonia 9:1. The product was recrystallized in acetonitrile. Yield: 14.4 g (67%) of rac-cis-4b-(2-amino-ethyl)-3-fluoro-4b,5,6,7,8,8a,9,10-octahydro-phenanthren-8a-ol as white crystals; m.p. 148°–149° C.

1.5. rac-cis-4b-(2-Amino-ethyl)-3-fluoro-4b,5,6,7,8,8a,9,10-octahydro-phenanthren-8a-ol (8.81 g, 0.003 mol) was dissolved in 10 ml of methanol. A 4.89N ethanolic HCl solution (0.63 ml, 0.003 mol) was added dropwise and the mixture was concentrated. The residue crystallized from ether. Yield: 0.68 g (74%) of rac-cis4b-(2-amino-ethyl)-3-fluoro-4b,5,6,7,8,8a,9,10-octahydro-phenanthren-8a-ol hydrochloride as white crystals; m.p. 233°–235° C.

EXAMPLE 2

2.1 39.4 g of potassium tert-butylate (0.35 mol) were added portionwise at −78° C. to a solution of 31.7 g of 7-chloro-1,2,3,4-tetrahydro-naphthalen-1-one (0.17 mol) in 500 ml of THF while gassing with argon. The mixture was stirred at −78° C. for 2 hrs. and then a solution of 35.8 ml of 1,4-dibromobutane (65.4 g, 0.3 mol) in 100 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with hexane/toluene 1:1. Yield: 29.8 g (86%) of 7'-chloro-3'4'-dihydro-spiro[cyclopentane-1,2'(1'H)-naphthalen]-1'-one as a colourless liquid.

MS: m/e (% basic peak)=234 ($C_{14}H_{15}ClO^+$, 22), 193 (100), 165 (12), 152 (19), 124 (19),89(18).

2.2. 116 g of methyltriphenylphosphonium bromide/sodium amide mixture (0.494 mol) were stirred for 3/4 hr. in 1l of THF at RT under argon. A solution of 29.8 g of 7'-chloro-3'4'-dihydrospiro[cyclopentane-1,2'(1'H)-naphthalen]-1'-one (0.127 mol) in 100 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off, concentrated and the residue was chromatographed over silica gel with toluene. Yield: 26.1 g (88%) of 7'-chloro-1'-methylene-3'4'-dihydro-spiro[cyclopentane-1,2'(1'H)-naphthalene] as a colourless liquid.

MS: m/e (% basic peak)=232 ($C_{15}H_{17}Cl^+$, 21), 217 (5), 191 (100), 175 (12), 153 (8), 141(8),115(10).

2.3. A solution of 11.9 ml of chlorosulphonyl isocyanate (0.13 mol) in 30 ml of ether was added dropwise at −78° C. while gassing with argon to a solution of 26.1 g of 7'-chloro-1'-methylene-3'4'-dihydro-spiro[cyclopentane-1,2'(1'H)-naphthalene] (0.11 mol) in 260 ml of ether. The mixture was stirred at-78° C. for 15 min., left to warm to RT and stirred for a further 15 hrs. The resulting crystallizate was filtered off under suction, washed with ether and dried in vacuo. Yield: 26.2 g (63%) of rac-cis-8-chloro-1,2,4,5-tetrahydro-3a,9b-butano-naphtho[2,1-b]furan-2-ylidene-sulphamoyl chloride [(E) or (Z) or (E/Z) mixture] as yellowish crystals; m.p. 192°–194° C.

2.4. 13.3 g (0.35 mol) of lithium aluminium hydride were suspended in 350 ml of dioxan under argon. A solution of 26.2 g of rac-cis-8-chloro-1,2,4,5-tetrahydro-3a,9b-butano-naphtho[2,1-b]-furan-2-ylidene-sulphamoyl chloride [(E) or (Z) (E/Z) mixture] (0.070 mol) in 800 ml of THF was added dropwise and the mixture was boiled under reflux for 16 hrs. 70 ml of ethyl acetate, 14 ml of water, 14 ml of a 15 percent aqueous NaOH solution and 42 ml of water were cautiously added dropwise in succession at ~40° C. to form a complete white precipitate. After filtration and concentration the residue was chromatographed over silica gel with methanol/ammonia 99:1. The product was suspended in ether, filtered off under suction, washed with ether and dried in vacuo. Yield: 6.9 g (35%) of rac-cis-4b-(2-amino-ethyl)-3-chloro4b,5,6,7,8,8a,9,10-octahydro-phenanthren-8a-ol as white crystals; m.p. 143°–145° C.

2.5. rac-cis-4b-(2-Amino-ethyl)-3-chloro-4b,5,6,7,8,8a,9,10-octahydro-phenanthren-8a-ol (1.54 g, 0.0055 mol) was dissolved in 50 ml of methanol. A 4.89N ethanolic HCl solution (1.12 ml, 0.0055 mol) was added dropwise and the mixture was concentrated. The residue crystallized from ether. Yield: 1.56 g (90%) of rac-cis4b-(2-amino-ethyl)-3-chloro-4b,5,6,7,8, 8a, 9,10-octahydro-phenanthren-8a-ol hydrochloride as white crystals; m.p. 280°–282° C.

EXAMPLE 3

3.1. 14.2 g of potassium tert-butylate (0.126 mol) were added portionwise at −78° C. to a solution of 14.2 g of 7-bromo-1,2,3,4-tetrahydro-naphthalen-1-one (0.063 mol) in 250 ml of THF while gassing with argon. The mixture was stirred at −78° C. for 2 hrs. and then a solution of 12.7 ml of 1,4-dibromobutane (23.1 g, 0.107 mol) in 250 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with toluene. Yield: 9.81 g (56%) of 7'-bromo-3'4'-dihydrospiro[cycyclopentane-1,2'(1'H)-naphthalen]-1'-one as yellowish oil.

MS: m/e (% basic peak)=278, 280 ($C_{14}H_{15}BrO^{30}$, 21), 237, 239 (100), 196, 198 (17), 168, 170 (20),128, 130(18), 89 (34).

3.2. 38.1 g of methyltriphenylphosphonium bromide/sodium amide mixture (0.091 mol) were stirred for 3/4 hr. in 380 ml of THF at RT under argon. A solution of 11.7 g of 7'-bromo-3'4'-dihydro-spiro[cyclopentane-1,2'(1'H)-naphthalen]-1'-one (0.042 mol) in 140 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off and concentrated. The residue was chromatographed over silica gel with petroleum ether. Yield: 84.2 g (77%) of 7'-bromo-1'-methylene-3'4'-dihydro-spiro[cyclopentane-1,2'(1'H)-naphthalene] as a yellowish oil.

MS: m/e (% basic peak)=276, 278 ($C_{15}H_{17}Br^{30}$, 19), 235, 237 (100), 219, 221 (8), 156 (20), 141 (23), 128 (27), 115 (26).

3.3. A solution of 3.02 ml of chlorosulphonyl isocyanate (0.034 mol) in 30 ml of ether was added dropwise at −78° C. while gassing with argon to a solution of 8.42 g of 7'-bromo-1'-methylene-3'4'-dihydro-spiro[cyclopentane-1,2 '(1H)-nampthalene] (0.029 mol) in 85 ml of ether. The mixture was stirred at −78° C. for 15 min., left to warm to RT and stirred for a f r 16 hrs. The resulting crystallizate was filtered off under suction, washed with ether and dried in vacuo. Yield: 5.08 g (42%) of rac-cis-8-bromo-1,2,4,5-tetrahydro-3a,9b-butano-naphtho[2,1-b]furan-2-ylidene-sulphamoyl chloride [(E) or (Z) or (E/Z) mixture] as yellowish crystals; m.p. 19520 -197C.

3.4. 1.19 g (0.054 mol) of lithium borohydride were suspended in 95 ml of dioxan under argon. A solution of 5.08 g of rac-cis-8-bromo-1,2,4,5-tetrahydro-3a,9b-butano-naphtho[2,1-b]furan-2-ylidene-sulphamoyl chloride [(E) or (Z) or (E/Z) mixture] (0.012 mol) in 250 ml of THF was added dropwise and the mixture was boiled under reflux for 16 hrs. 1.2 ml of water, 1.2 ml of a 15 percent aqueous NaOH solution and 3.6 ml of water were cautiously added dropwise in succession at RT such a complete white precipitate. After filtration and concentration the residue was chromatographed over silica gel with isopropyl alcohol/ammonia 19:1. The product crystallized from acetonitrile. Yield: 1.29 g (33%) of rac-cis-4b-(2-amino-ethyl)-3-bromo-4b,5,6,7,8,8,a,9,10-octahydro-phenanthren-8a-ol as white crystals; m.p. 135°–136° C.

3.5. rac-cis-4b-(2-Amino-ethyl)-3-bromo-4b,5,6,7,8,8a,9,10-octahydro-phenanthren-8a-ol hydrochloride a white crystals; m.p. 20 ml of methanol. A 4.89N ethanolic HCl solution (0.36 ml, 0.0017 tool) was added dropwise and the mixture was concentrated. The residue crystallized from ethanol/ether. Yield: 0.23 g (37%) of rac-cis-4b-(2-amino-ethyl)-3-bromo-4b,5,6,7,8,8a,9,10-octahydro-phenanthren-8a-ol hydrochloride as white crystals; m.p. 283°–286° C.

EXAMPLE 4

4.1 10.2 g of potassium tert-butylate (0.090 mol) were added portionwise at −78C. to a solution of 12.3 g of 7-iodo-l,2,3,4-tetrahydro-naphthalen-1-one (0.045 mol) in 200 ml of THF while gassing with argon. The mixture was stirred at −78o(2; for 2 hrs. and then a solution of 9.25 ml of 1,4-dibromobutane (16.9 g, 0.078 mol) in 25 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO4, filtered off, concentrated and the residue was chromatographed over silica gel with toluene. Yield: 8.67 g (59%) of 7'-iodo-3'4'-dihydro-spiro[cyclopentane-1,2'(1'H)-naphthalen]-1'-one as a colourless liquid.

MS: m/e (% basic peak)=326 ($C_{14}H_{15}IO^+$, 30), 285 (100), 243 (14), 21(12), 89 (14).

4.2. 24.4 g of methyltriphenylphosphonium bromide/sodium amide mixture (0.058 mol) were stirred for 3/4 hr. in 200 ml of THF at RT under argon. A solution of 7.19 g of 7'-iodo-3'4'-dihydro-spiro-[cyclopentane-1,2'(1'H)-naphthalen]1'-one (0.027 mol) in 50 ml of THF was added dropwise to the yellow suspension and the mixture was then stirred for 18 hrs. Water was added, the mixture was extracted with ether, the organic phase was washed with a saturated aqueous sodium chloride solution, dried over MgSO4, filtered off and concentrated. The residue was chromatographed over silica gel with toluene. Yield: 8.16 g (95%) of 7'-iodo-1'-methylene-3'4'-dihydro-spiro[cyclopentane-1,2'(1'H)-naphthalene] as a yellowish oil.

MS: m/e (% basic peak)=324 ($C_{15}H_{17}I^+$, 25), 283 (100), 156 (11), 141 (15), 128 (16), 115 (15).

4.3. A solution of 2.6 ml of chlorosulphonyl isocyanate (0.030 mol)in 20 ml of ether was added dropwise at −78° C. while gassing with argon to a solution of 8.16 g of 7'-iodo-1'-methylene-3'4'-dihydro-spiro[cyclopentane-1,2'(1'H)-naphthalene] (0.025 mol) in 80 ml of ether. The mixture was stirred at −78° C. for 15 min., left to warm to RT and stirred for a further 16 hrs. The resulting crystallizate was filtered off under suction, washed with ether and dried in vacuo. Yield: 6.64 g (57%) of rac-cis-1,2,4,5-tetrahydro-8-iodo-3a,9b-butano-naphtho[2,1 -b]furan-2-ylidene-sulphamoyl chloride [(E) or (Z) or (E/Z) mixture] as yellowish crystals; m.p. 190°–192° C.

4.4. 1.53 g (0.07 mol) of lithium borohydride were suspended in 100 ml of dioxan under argon. A solution of 6.38 g of rac-cis-1,2,4,5-tetrahydro-8-iodo-3a,9b-butano-naphtho[2,1-b]furan-2-ylidene-sulphamoyl chloride [(E) or (Z) or (E/Z) mixture] (0.014 mol) in 100 ml of THF was added dropwise and the mixture was boiled under reflux for 2 hrs. 1.5 ml of water, 1.5 ml of a 15 percent aqueous NaOH solution and 4.5 ml of water were cautiously added dropwise in succession at RT to form a complete white precipitate. After filtration and concentration the residue was chromatographed over silica gel with methanol/ammonia 99:1. The product was suspended in ether, filtered off under suction, washed with ether and dried in vacuo. Yield: 1.43 g (28%) of rac-cis-4b-(2-amino-ethyl)-3-iodo-4b,5,6,7,8,8a,9,10-octahydro-phenanthren-8a-ol as white crystals; m.p. 144°–146° C.

4.5. rac-cis-4b-(2-Amino-ethyl)-3-iodo-4b,5,6,7,8,8a,9,10-octahydro-phenanthren-8a-ol (1.39 g, 0.0037 mol) was dissolved in 40 ml of methanol. A 4.89N ethanolic HCl solution (0.78 ml, 0.0037 mol) was added dropwise and the mixture was concentrated. The residue crystallized from ethanol/ether. Yield: 1.26 g (83%) of rac-cis-4b-(2-amino-ethyl)-3-iodo-4b,5,6,7,8,8a,9,10-octahydro-phenanthren-8a-ol hydrochloride as white crystals; m.p. 271°–273° C.

EXAMPLE 5

5.1. 88.5 g of potassium tert-butylate (0.79 mol) were added portionwise at −78° C. to a solution of 99.5 g of 7-benzyloxy-1,2,3,4-tetrahydro-naphthalen-1-one (0.39 mol) in 1 l of THF while gassing with argon. The mixture was stirred at −78° C. for 2 hrs. and then a solution of 80 ml of 1,4-dibromobutane (146 g, 0.67 mol) in 100 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO4, filtered off, concentrated and the residue was chromatographed over silica gel with hexane/ethyl acetate 9:1. After vigorous in hexane there was obtained a suspension which was filtered off under suction and dried in vacuo. yield: 48.5 g (77%) of 7'-benzyloxy-3'4'-dihydro-spiro[cyclopentane-1,2'(1'H)-naphthalen]-1-one as white crystals; m.p. 61°–63C.

5.2. 84.9 g of methyltriphenylphosphonium bromide/sodium amide mixture (0.2 mol) were stirred for 3/4 hr. in 840 ml of THF at RT under argon. A solution of 28.6 g of 7'-benzyloxy-3'4'-dihydro-spiro[cyclopentane-1,2'(1'H)-naphthalen]-1'-one (0.093 mol)in 100 ml of THF was added dropwise to the yellow suspension and the mixture was then stirred for 18 hrs. Water was added, the mixture was extracted with ether, the organic phase was washed with a saturated sodium chloride solution, dried over MgSO4, filtered off and concentrated. The product was distilled using a bulb-tube apparatus. Yield: 28.7 g (100%) of 7'-benzyloxy-1'-methylene-3'4'-dihydro-spiro[cyclopentane-1,2'(1'H)-naphthalene] as a colourless liquid; p.p. 230°–250° C./0.04 Torr.

5.3. A solution of 8.5 ml of chlorosulphonyl isocyanate (0.097 mol) in 50 ml of ether was added dropwise at −78° C. while gassing with argon to a solution of 25.7 g of 7'-benzyloxy-1'-methylene-3'4'-dihydro-spiro[cyclopentane-1,2'(1'H)-naphthalene] (0.084 mol)in 300 ml of ether. The mixture was stirred at −78° C. for 15 min. and left to warm to RT within 1 hr. The resulting crystallizate was filtered off under suction, washed with ether and dried in vacuo. Yield: 26.6 g (70%) of rac-cis-8-benzyloxy-1,2,4,5-tetrahydro-3a,9b-butano-naphtho[2,1-b]furan-2-ylidine-sulpyhamoyl chloride [(E) or (Z) or (E/Z) mixture] as yellowish crystals; m.p. 191°–192° C.

5.4 22.4 g (0.59 mol) of lithium aluminium hydride were suspended in 800 ml of dioxan under argon. A solution of 52.7 g of rac-cis-8-benzyloxy-1,2,4,5-tetrahydro-3a,9b-butano-naphtho[2,1 b]furan-2-ylidene-sulphamoyl chloride [(E) or (Z) or (E/Z) mixture] (0.12 mol) in 2.2l of THF was added dropwise and the mixture was boiled under reflux for 24 hrs. 22.4 ml of water, 22.4 ml of a 15 percent aqueous NaOH solution and 67.2 ml of water were cautiously added dropwise in succession at RT to form a complete white precipitate. After filtration and concentration the residue was chromatographed over silica gel with methanol. The product was recrystallized from acetonitrile and dried in vacuo. Yield: 18.7 g (45%) of rac-cis-4b-(2-amino-ethyl)-3-benzyloxy-4b,5,6,7,8,8a, 9,10-octahydro-phenanthren-8a-ol as white crystals; m.p. 162°–163° C.

5.5. 29 g of rac-cis-4b-(2-aminoethyl)-3-benzyloxy-4b,5,6,7,8,8a,9,10-octahydro-phenanthren-8a-ol (0.0825 mol) were dissolved in 550 ml of ethyl formate and 35 ml of formic acid. The mixture was boiled under reflux for 130 hrs., concentrated and chromatographed over silica gel with methanol/ammonia 19:1. The product crystallized from THF/acetonitrile. Yield: 17.6 g (56%) of rac-cis-N-[2-(6-benzyloxy-10a-hydroxy-1,2,3,4,4a,9,10,10a-octahydro-phenanthren-4a-yl)-ethyl]-formamide as white crystals; m.p. 137°–138° C.

5.6. 4.8 g (0.12 mol) of lithium aluminium hydride were suspended in 600 ml of THF under argon. A solution of 17.6 g of rac-cis-N-[2(6-benzyloxy-10a-hydroxy-1,2,3,4,4a,9,10,10a-octahydro-phenanthren-4a-yl)-ethyl]-formamide (0.046 mol) in 200 ml of THF was added dropwise thereto and the mixture was boiled under reflux for 5 hrs. A mixture of 20 ml of water and 100 ml of THF was cautiously added dropwise to form a complete white precipitate. After filtration and concentration the residue was chromatographed over silica gel with CH$_2$Cl$_2$/methanol/ammonia 90:9:1. The product crystallized from hot hexane. Yield: 13.1 g (77%) of rac-cis-3-benzyloxy-4b-(2-methylamino-ethyl)-4b,5,6,7,8,8a,9,10-octahydro-phenanthren-8a-ol as white crystals; m.p 107°–109√ C.

5.7. 2.04 g of rac-cis-3-benzyloxy-4b-(2-methylamino-ethyl)-4b,5,6,7,8,8a,9,10-octahydro-phenanthren-8a-ol (0.005 mol) were dissolved in 150 ml of ethanol. After the addition of 0.55 g of 10 percent Pd—C catalyst the mixture was hydrogenated for 1 hr. at RT under 1 atm. The mixture was filtered and the filtrate was concentrated. The product crystallized from methanol. Yield: 1.04 g (68%) of rac-cis-4b-(2-methylamino-ethyl)-4b,5,6,7,8,8a,9,10-octahydro-phenanthrene-3,8a-diol as white crystals; m.p. 200°–201° C.

5.8. rac-cis-4b-(2-Methylamino-ethyl)-4b,5,6,7,8,8a,9,10-octahydro-phenanthrene-3,8a-diol (1 g, 0.0036 mol) was dissolved in 25 ml of methanol. A 1N ethanolic HCl solution (3.65 ml, 0.0036 mol) was added dropwise and the mixture was concentrated. The residue crystallized from ethanol. Yield: 0.58 g (51%) of rac-cis-4b-(2-methylamino-ethyl)-4b,5,6,7,8,8a,9,10-octahydro-phenanthrene-3,8a-diol hydrochloride as white crystals; m.p. 215°–216C.

EXAMPLE 6

6.1. 38.2 g of potassium tert-butylate (0.34 mol) were added portionwise at −78° C. to a solution of 30 g of 7-methoxy-1,2,3,4-tetrahydro-naphthalen-1 -one (0.17 mol) in 350 ml of THF while gassing with argon. The mixture was stirred at −78° C. for 2 hrs. and then a solution of 34.2 ml of 1,4-dibromobutane (62.4 g, 0.289 mol) in 150 ml of THF was added dropwise. The cooling bath was removed and the mixture was stirred at RT for 16 hrs. Water was added thereto, the mixture was extracted with ether, the organic phase was washed with saturated aqueous sodium chloride solution, dried over MgSO$_4$, filtered off, concentrated and the residue was chromatographed over silica gel with hexane/ether 3:2. The product was distilled through a 20 cm Vigreux column. Yield: 32 g (82%) of 3'4'-dihydro-7'-methoxy-spiro-[cyclopentane-1,2'(1'H)-naphthalen]-1'-one as a colourless liquid; b.p. 140° C./5 Torr.

6.2. 100 g of methyltriphenylphosphonium bromide/sodium amide mixture (0.24 mol) were stirred for 3/4 hr. in 500 ml of THF at RT under argon. A solution of 46 g of 3'4'-dihydro-7'-methoxy-spiro [cyclopentane-1,2'(1'H)-naphthalen]-1'-one (0.20 mol) in 100 ml of THF was added dropwise to the yellow suspension and the mixture was then stirred for 18 hrs. Water was added thereto, the mixture was extracted with ether, the organic phase was washed with a saturated aqueous sodium chloride solution, dried over MgSO$_4$, filtered off and concentrated. The residue was suspended in 300 ml of hot hexane, cooled to 0° C. and filtered off (the filter cake consisted of triphenylphosphine oxide). The product was chromatographed over silica gel with hexane/ether 3:2 and distilled through a 20 cm Vigreux column. Yield: 33 g (72%) of 7'-methoxy-1'-methylene-3'4'-dihydro-spiro[cyclopentane-1,2'(1 'H)-naphthalene] as a colourless liquid; b.p. 155° C./9 Torr.

6.3. 15.2 ml of chlorosulphonyl isocyanate (0.173 mol) were added dropwise at −78° C. while gassing with argon to a solution of 33 g of 7'-methoxy-1'-methylene-3'4'-dihydro-spiro[cyclopentane-1,2'(1 'H)-naphthalene] (0.145 mol) in 300 ml of ether. The mixture was stirred at −78° C. for 15 min. and left to warm to RT within 1 hr. The resulting crystallizate was filtered off under suction, washed with ether and dried in vacuo. Yield: 24 g (45%) of rac-cis-1,2,4,5-tetrahydro-8-methoxy-3a,9b-butano-naphtho[2,1-b]furan-2-ylidene-sulphamoyl chloride [(E) or (Z) or (E/Z) mixture] as yellowish crystals; m.p. 152°–153° C.

6.4. 2.57 g (0.068 mol) of lithium aluminium hydride were suspended in 80 ml of dioxan under argon. A solution of 5 g of rac-cis-1,2,4,5-tetrahydro-8-methoxy-3a,9b-butano-naphtho[2,1-b]furan-2-ylidene-sulphamoyl chloride [(E) or (Z) or (E/Z) mixture] (0.014 mol) in 80 ml of THF was added dropwise at ∼45° C. and the mixture was boiled under reflux for ½ hr. 2.6 ml of water, 3.0 ml of a 15 percent aqueous NaOH solution and 2.6 ml of water were cautiously added dropwise in succession at RT to form a complete white precipitate. After filtration and concentration the product was crystallized from hexane/ether. Yield: 2.3 g (62%) of rac-cis-4b-(2-amino-ethyl)-3-methoxy-4b ,5,6,7,8,8a,9,10-octahydro-phenanthren-8a-ol as white crystals; 103°–106° C.

EXAMPLE 7

7.1. 20.3 g of potassium tert-butylate (0.181 mol) were added portionwise at −78° C. to a solution of 26.8 g of 5-benzyloxy-1,2,3,4-tetrahydro-naphthalen-1-one (0.106mol) in 270 ml of THF while gassing with argon. The mixture was stirred at −78° C. for 2 hrs. and then a solution of 25.2 ml of 1,4-dibromobutane (45.9 g, 0.212 mol) in 60 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with hexane/ethyl acetate 9:1. Yield: 11.8 g (36%) of 5′-benzyloxy-3′4′-dihydro-spiro[cyclopentane-1,2′(1′H)-naphthalen]-1′-one as a solid material; m.p. 67°–70° C.

7.2. 61.6 g of methyltriphenylphosphonium bromide/sodium amide mixture (0.148 mol) were stirred for ¾ hr. in 600 ml of THF at RT under argon. A solution of 20.5 g of 5′-benzyloxy-3′4′-dihydro-spiro-[cyclopentane-1,2′(1′H)-naphthalen]-1′-one (0.0672 mol) in 200 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off, concentrated and the residue was chromatographed over silica gel with hexane/ether 3:1. Yield: 19.8 g (97%) of 5′-benzyloxy-1′-methylene-3′4′-dihydro-spiro-[cyclopentane-1,2′(1′H)-naphthalene] as a yellowish oil.

MS: m/e (% basic peak)=304 (C$_{22}$H$_{24}$O$^+$, 8,5), 263 (17), 212 (2), 171 (1) 115 (2), 91 (100). 7.3. A solution of 0.62 ml of chlorosulphonyl isocyanate (0.0071 mol) in 10 ml of ether was added dropwise at −78° C. while gassing with argon to a solution of 1.80 g of 5′-benzyloxy-1′-methylene- 3′4′-dihydro-spiro-[cyclopentane-1,2′(1 ′H)-naphthalene] (0.0059 mol) in 20 ml of ether. The mixture was stirred at −78° C. for 15 min. and left to warm to RT within 1 hr. The resulting crystallizate was filtered off under suction, washed with ether and dried in vacuo. Yield: 1.2 g (46%) of rac-cis-6-benzyloxy-1,2,4,5-tetrahydro-3a,9b-butano-naphtho[2,1-b]furan-2-ylidene-sulphamoyl chloride [(E) or (Z) or (E/Z) mixture] as off-white crystals; m.p. 167°–168° C.

7.4. 7.0 g (0.185 mol) of lithium aluminium hydride were suspended in 185 ml of dioxan under argon. A solution of 1.65 g rac-cis-6-benzyloxy-1,2,4,5-tetrahydro-3a,9b-butano-naphtho[2,1 b]furan-2-ylidene-sulphamoyl chloride [(E) or (Z) or (E/Z)-mixture] (0.037 mol) in 340 ml of THF was added dropwise and the mixture was boiled under reflux for 19 hrs. 50 ml of ethyl acetate, 7 ml of water, 14 ml of a 15 percent aqueous NaOH solution and 7 ml of water were cautiously added dropwise in succession at ∼40° C. to form a complete white precipitate. After filtration and concentration the residue was chromatographed over silica gel with methanol/ammonia. The product was suspended in ether, filtered off under suction, washed with ether and dried in vacuo. Yield: 3.8 g.(29%) of rac-cis-4b-(2-amino-ethyl)-1-benzyloxy-4b,5,6,7,8,8a,9,10-octahydro-phenanthren-8a-ol as white crystals; m.p. 164°–165° C.

7.5. 3.8 g of rac-cis-4b-(2-amino-ethyl)-1-benzyloxy-4b,5,6,7,8,8a,9,10-octahydro-phenanthrene-1,8a-ol (0.0109 mol) were dissolved in 100 ml of methanol. After the addition of 0.6 g of 10 percent Pd—C catalyst the mixture was hydrogenated for 16 hrs. at RT under 1 atm. The mixture was filtered and the filtrate was concentrated. Yield: 2.9 g (90%) of rac-cis-4b-(2-amino-ethyl)-4b,5,6,7,8,8a,9,10-octahydro-phenanthrene-1,8a-diol as a white foam.

7.6. rac-cis-4b-(2-Amino-ethyl)-4b,5,6,7,8,8a,9,10-octahydro-phenanthrene-1,8a-diol (2.9 g, 0.0097 mol) was dissolved in 60 ml of ethanol. A 5N ethanolic HCl solution (2.3 ml, 11.6 mol) was added dropwise and the mixture was concentrated. After vigorous stirring in ether there was obtained a suspension which was suction filtered and dried in vacuo. Yield: 2.85 g (88%) of rac-cis-4b-(2-amino-ethyl)-4b,5,6,7,8,8a,9,10-octahydro-phenanthrene-1,8a-diol hydrochloride as white crystals (88%) with m.p. 244°246° C.

EXAMPLE 8

8.1. 3.8 g of potassium tert-butylate (0.0338 mol) were added portionwise at −78° C. to a solution of 5.0 g of 6-benzyloxy-1,2,3,4-tetrahydro-naphthalen-1-one (0.0198 mol) in 50 ml of THF while gassing with argon. The mixture was stirred at −78° C. for 2 hrs. and then a solution of 4.7 ml of 1,4-dibromobutane (8.55 g, 0.0396 mol) in 50 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with toluene. The product was recrystallized from hexane/ether and dried in vacuo. Yield: 2.0 g (33%) of 6′-benzyloxy-3′4′-dihydro-spiro-[cyclopentane-1,2′(1′H)naphthalen]-1′-one as white crystals; m.p. 79°–81 ° C.

8.2. 5.9 g of methyltriphenylphosphonium bromide/sodium amide mixture (0.0143 mol) were stirred for ¾ hr. in 60 ml of THF at RT under argon. A solution of 2.0 g of 6′-benzyloxy-3′4′-dihydro-spiro-[cyclopentane-1,2′(1′H)-naphthalen]-1′-one (0.0065 mol) in 20 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off, concentrated and the residue was chromatographed over silica gel with hexane/ether 9:1. Yield: 1.8 g (91%) of 6′-benzyloxy-1′-methylene-3′4′as a yellowish solid; m.p. 64°–65° C.

8.3. A solution of 0.62 ml of chlorosulphonyl isocyanate (0.0071 mol) in 10 ml of ether was added dropwise at −78° while gassing with argon to a solution of 1.8 g of 6′-benzyloxy-1′-methylene-3′4′-dihydro-spiro[cyclopentane-1,2′(1′H)-naphthalene] (0.0059 mol) in 60 ml of ether. The mixture was stirred at −78° for 15 min. and left to warm to RT within 1 hr. The mixture was concentrated and the resulting foam was recrystallized from ether. Yield: 1.3 g (49%) of rac-cis-7-benzyloxy-1,2,4,5-tetrahydro-3a,9b-butano-naphtho[2,1 -b]furan-2-ylidene-sulphamoyl chloride [(E) or (Z) or (E/Z) mixture] as white crystals; m.p. 155°–157° C. 0.

8.4. 8.6 g (0.227 mol) of lithium aluminium hydride were suspended in 230 ml of dioxan under argon. A solution of 20.3 g of rac-cis-7-benzyloxy-1,2,4,5-tetrahydro-3a,9b-butano-naphtho[2,1-b]furan-2-ylidene-sulphamoyl chloride [(E) or (Z) or (E/Z) mixture] (45.3 mol) in 600 ml of dioxan was added dropwise and the mixture was boiled under reflux for 24 hrs. 60 ml of ethyl acetate, 9 ml of water, 9 ml of a 15 percent aqueous NaOH solution and 18 ml of water were cautiously added dropwise in succession at ∼40° C. to form a complete white precipitate. After filtration and concentration the residue was chromatographed over silica gel with methanol/ammonia 19:1. The product was suspended in ether, filtered off under suction washed with ether and dried in vacuo. Yield: 2.1 g (13%) of rac-cis-4b-(2-amino-ethyl)-2-benzyloxy-4b,5,6,7,8,8a,9,10-octahydro-phenanthren-8a-ol as white crystals; m.p. 125°–128° C.

8.5. 2.8 g of rac-cis-4b-(2-amino-ethyl)-2-benzyloxy-4b,5,6,7,8,8a,9,10-octahydro-phenanthren-8a-ol (0.008 mol) were dissolved in 80 ml of methanol. After the addition of 0.28 g of 10 percent Pd—C catalyst the mixture was hydrogenated for 16 hrs. at RT under 1 atm. The mixture was filtered and the filtrate was concentrated. Yield: 2.0 g (96%) of rac-cis-4b-(2-amino-ethyl)-4b,5,6,7,8,8a,9,10-octahydro-phenanthrene-2,8a-diol as a white foam.

8.6. rac-cis-4b-(2-Amino-ethyl)-4b,5,6,7,8,8a,9,10-octahydro-phenanthrene-2,8a-diol (2.0 g, 0.067 mol) was dissolved in 40 ml of methanol. A 5N ethanolic HCl solution (1.6 ml, 0.008 mol) was added dropwise and the mixture was concentrated. Yield: 2.3 g (97%) of rac-cis-4b-(2-amino-ethyl)-4b,5,6,7,8,8a,9,10-octahydro-phenanthrene-2,8a-diol hydrochloride as a white foam.

MS: m/e (% basic peak)=261 ($C_{16}H_{23}NO_{2+}$, 16), 217 (43), 199 (79), 187 (31), 173 (20), 157 (37), 133 (20), 107 (22), 45 (90), 30 (100).

EXAMPLE 9

9.1. 0.95 g of potassium tert-butylate (0.085 mol) was added portionwise at −78° C. to a solution of 1.3 g of 8-benzyloxy-1,2,3,4-tetrahydro-naphthalen-1-one (0.005 mol) in 15 ml of THF while gassing with argon. The mixture was stirred at −78° C. for 2 hrs. and then a solution of 1.2ml of 1,4-dibromobutane (2.15 g, 0.010 mol) in 6 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO4, filtered off, concentrated and the residue was chromatographed over silica gel with hexane/ethyl acetate 9:1. Yield: 0.5 g (33%) of 8′-benzyloxy-3′4′-dihydro-spiro[cyclopentane-1,2′(1′H)-naphthalen]-1′-one as a yellowish liquid.

MS: m/e (% basic peak)=306 ($C_{21}H_{22}O_{2+}$, 10), 288 (1), 265 (2), 224 (6), 197 (3), 159 (6), 91(100).

9.2. 69 g of methyltriphenylphosphonium bromide/sodium amide mixture (0.166 mol) were stirred for ¾ hr. in 700 ml of THF at RT under argon. A solution of 20.3 g of 8′-benzyloxy-3′4′-dihydro-spiro[cyclopentane-1,2′(1′H)-naphthalen]-1′-one (0.0663 mol) in 200 ml of THF was added dropwise to the yellow suspension and the mixture was then stirred for 18 hrs. Water was added, the mixture was extracted with ether, the organic phase was washed with a saturated aqueous sodium chloride solution, dried over MgSO4, filtered off, concentrated and the residue was chromatographed over silica gel with hexane. Yield: 11.2 g (55%) of 8′-benzyloxy-1′-methylene-3′4′-dihydro-spiro[cyclopentane-1,2′(1′H)-naphthalene] as a yellowish liquid.

MS: m/e (% basic peak)=304 ($C_{22}H_{24}O^{30}$, 5.6), 263 (3.2), 222 (39), 213 (27), 200 (10), 131, (79), 91, (100).

9.3. A solution of 0.62 ml of chlorosulphonyl isocyanate (0.0071 mol) in 6 ml of ether was added dropwise at −78° C. while gassing with argon to a solution of 1.80 g of 8′-benzyloxy-1′-methylene-3′4′-dihydro-spiro[cyclopentane-1,2′(1′H)-naphthalene] (0.0059 mol) in 60 ml of ether. The mixture was stirred at −78° C. for 15 min. and left to warm to RT within 1 hr. The resulting crystallizate was filtered off under suction, washed with ether and dried in vacuo. Yield: 1.2 g (46%) of rac-cis-9-benzyloxy-1,2,4,5-tetrahydro-3a,9b-butano-naphtho[2,1-b]furan-2-ylidene-sulphamoyl chloride [(E) or (Z) or (E/Z) mixture] as off-white crystals; m.p. 135°–137° C.

9.4. 4.4 g (0.116 mol) of lithium aluminium hydride were suspended in 115 ml of dioxan under argon. A solution of 10.3 g of rac-cis-9-benzyloxy-1,2,4,5-tetrahydro-3a,9b-butano-naphtho[2,1-b]furan-2-ylidene-sulphamoyl chloride [(E) or (Z) or (E/Z) mixture] (0.0231 mol) in 200 ml of dioxan/THF 1:1 was added dropwise thereto and the mixture was boiled under reflux for 20 hrs. 50 ml of ethyl acetate, 4 ml of water, 4 ml of a 15 percent aqueous NaOH solution and 12 ml of water were cautiously added dropwise in succession at ∼40° C. to form a complete white precipitate. After filtration and concentration the residue was chromatographed over silica gel with methanol/ammonia 9:1. A sample was recrystallized from ether/hexane at −20° C. Yield: 3.55 g (44%) of rac-cis-4b-(2-amino-ethyl)-4-benzyloxy-4b,5.6.7.8.8a,9,10-octahydro-phenanthren-8a-ol as a white foam and white crystals; m.p. 106°–108° C.

9.5. 3.5 g of rac-cis-4b-(2-amino-ethyl)-4-benzyloxy-4b,5,6,7,8,8,a,9,10-octahydro-phenanthren-8a-ol (0.00995 mol) were dissolved in 100 ml of methanol. After the addition of 0.35 g of 10 percent Pd—C catalyst the mixture was hydrogenated for 70 hrs. at RT under 1 atm. The mixture was filtered and the filtrate was concentrated. Yield: 2.66 g (100%) of rac-cis-4b-(2-amino-ethyl)-4b,5,6,7,8,8a,9,10-octahydro-phenanthrene-4,8a-diol as a white foam.

MS: m/e (% basic peak)=261 ($C_{16}H_{23}NO^{2+}$, 18), 244 (14), 226 (29), 199 (4), 187 (30), 173 (21), 157 (23), 145 (25), 133 (21), 30 (100).

9.6. rac-cis-4b-(2-Amino-ethyl)-4b,5,6,7,8,8a,9,10-octahydro-phenanthrene-4,8a-diol (2.66 g, 0.0101 mol) was dissolved in 60 ml of ethanol. A 5N ethanolic HCl solution (2.5 ml, 0.0125 mol) was added dropwise and the mixture was concentrated. The residue crystallized from ethanol. Yield: 2.62 g (87%) of rac-cis-4b-(2-amino-ethyl)-4b,5,6,7,8,8a,9,10-octahydro-phenanthrene-4,8a-diol hydrochloride as white crystals; m.p. 248°–249° C.

EXAMPLE 10

10.1.93.8 g of potassium tert-butylate (0.837 mol) were added portionwise at −78° C. to a solution of 75.6 g of 5-chloro-1,2,3,4-tetrahydro-naphthalen-1-one (0.419 mol) in 760 ml of THF while gassing with argon. The mixture was stirred at −78° C. for 2 hrs. and then a solution of 84 mi of 1,4-dibromobutane (134 g, 0.711 mol) in 350 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO4, filtered off, concentrated and the residue was chromatographed over silica gel with hexane/toluene 1:1. Yield: 54.4 g (55%) of 5′-chloro-3′4′-dihydro-spiro[cyclopentane-1,2′(1′H)-naphthalen]-1′-one as a colourless oil.

MS: m/e (% basic peak)=234 ($C_{14}H_{15}ClO^+$, 21), 193 (100), 165 (13), 152 (21), 124 (14), 89 (14).

10.2. 211 g of methyltriphenylphosphonium bromide/sodium amide mixture (0.506 mol) were stirred for 182 hr. in 1l of THF at RT under argon. A solution of 54.4 g of 5′-chloro-3′4′-dihydro-spiro[cyclopentane-1,2′(1′H)-naphthalen]-1′-one (0.232mol) in 500 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off, concentrated and the residue was chromatographed over silica gel with petroleum ether. Yield: 40.5 g (75%) of 5'-chloro-1'-methylene-3'4'-dihydro-spiro[cyclopentane-1,2'(1'H)-naphthalene] as a yellowish oil.

MS: m/e (% basic peak)=232 ($C_{15}H_{17}Cl^+$, 18), 191 (100), 175 (13), 155 (8), 141 (10), 128 (10), 115 (11).

10.3. A solution of 18.2 ml of chlorosulphonyl isocyanate (0.209 mol) in 180 ml of ether was added dropwise at −78° C. while gassing with argon to a solution of 40.5 g of 5'-chloro-1'-methylene-3'4'-dihydro-spiro[cyclopentane-1,2'(1'H)-naphthalene] (0.173 mol) in 300 ml of ether. The mixture was stirred at −78° C. for 15 min. and left to warm to RT within 1 hr. The resulting crystallizate was filtered off under suction, washed with ether and dried in vacuo. Yield: 37.2 g (58%) of rac-cis-6-chloro-1,2,4,5-tetrahydro-3a,9b-butano-naphtho[2,1-b]furan-2-ylidene-sulphamoyl chloride [(E) or (Z) or (E/Z) mixture] as yellowish crystals; m.p. 179°–181° C.

10.4. 9.7 g (0.0447) of lithium borohydride were suspended in 200 ml of dioxan under argon. A solution of 37.2 g of rac-cis-6-chloro-1,2,4,5-tetrahydro-3a,9b-butano-naphtho[2,1-b]furan-2-ylidene-sulphamoyl chloride [(E) or (Z) or (E/Z) mixture] (0.099 mol) in 550 ml of THF was added dropwise and the mixture was boiled under reflux for 18 hrs. 10 ml of water, 10 ml of a 15 percent aqueous NaOH solution and 30 ml of water were cautiously added dropwise in succession at ∼40° C. to form a complete white precipitated resulted. After filtration and concentration the residue was chromatographed over silica gel with methanol/ammonia (19:1). The product was recrystallized from hot acetonitrile. Yield: 6.9 g (25%) of rac-cis-4b-(2-amino-ethyl)-1-chloro-4b,5,6,7,8a,9,10-octahydro-phenanthren-8a-ol as white crystals; m.p. 161°–162° C.

10.5. rac-cis-4b-(2-Amino-ethyl)-1-chloro-4b,5,6,7,8,8a,9,10-octahydro-phenanthren-8a-ol (6.9 g, 0.0248 mol) was dissolved in 200 ml of THF. A 5N ethanolic HCl solution (10 ml, 0.05 mol) was added dropwise and the resulting suspension was suction filtered. The product was recrystallized from ethanol/ether. Yield: 6.7 g (85%) of rac-cis-4b-(2-amino-ethyl)-1-chloro-4b,5,6,7,8,8a,9,10-octahydro-phenanthren-8a-ol hydrochloride as white crystals; m.p. 269°–271° C.

EXAMPLE 11

11.1. 42.2 g of potassium tert-butylate (0.377 mol) were added portionwise at −78° C. to a solution of 40 g of 6-chloro-1,2,3,4-tetrahydro-naphthalen-1-one (0.221 mol) in 400 ml of THF while gassing with argon. The mixture was stirred at −78° C. for 2 hrs. and then a solution of 52.4 ml of 1,4-dibromobutane (95.6 g, 0.443 mol) in 260 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with hexane/ethyl acetate 9:1. The product crystallized from hexane at −50° C. Yield: 15 g (29%) of 6'-chloro-3'4'-dihydro-spiro[cyclopentane-1,2'(1'H)-naphthalen]-1'-one as white crystals; m.p. 31°–33° C.

11.2. 97.6 g of methyltriphenylphosphonium bromide/sodium amide mixture (0.235 mol) were stirred for ¾hr. in 1 l of THF at RT under argon. A solution of 25 g of 6'-chloro-3'4'-dihydro-spiro[cyclopentane-1,2'(1'H)-naphthalen]-1'-one (0.107mol) in 250 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off and concentrated. The residue was suspended in 1 l of hot hexane, cooled to 0° C. and filtered off (the filter cake consisted of triphenylphosphine oxide). The product was chromatographed over silica gel with hexane. Yield: 22.7 g (92%) of 6'-chloro-1'-methylene-3'4'-dihydro-spiro[cyclopentane-1,2'(1'H)-naphthalene] as a yellowish liquid.

MS: m/e (% basic peak)=232 ($C_{15}H_{17}Cl^+$, 14), 191 (100), 175 (11), 153 (9), 141 (10), 128 (12), 115 (14).

11.3 A solution of 10.2 ml of chlorosulphonyl isocyanate (0.117 mol) in 100 ml of ether was added dropwise at −78° C. while gassing with argon to a solution of 22.6 g of 6'-chloro-1'-methylene-3'4'-dihydro-spiro[cyclopentane-1,2'(1'H)-naphthalene] (0.0971 mol) in 230 ml of ether. The mixture was stirred at −78° C. for 15 min. and left to warm to RT within 1 hr. The resulting crystallizate was filtered off under suction, washed with ether and dried in vacuo. Yield: 14.2 g (39%) of rac-cis-7-chloro-1,2,4,5-tetrahydro-3a,9b-butano-naphtho[2,1-b]furan-2-ylidene-sulphamoyl chloride [(E) or (Z) or (E/Z) mixture] as white crystals; m.p. 123°–125° C.

11.4. 7.2 g (0.189 mol) of lithium aluminium hydride in 190 ml of dioxan under argon. A solution of 14.1 g of rac-cis-7-chloro-1,2,4,5-tetrahydro-3a,9b-butano-naphtho[2,1-b]furan-2-ylidene-sulphamoyl chloride [(E) or (Z) or (E/Z) mixture] (0.0376 mol) in 280 ml of THF was added dropwise and the mixture was boiled under reflux for 20 hrs. 7 ml of water, 14 ml of 15 percent aqueous NaOH solution and 7 ml of water were cautiously added dropwise in succession at ∼40° C. so that a complete white precipitate. After filtration and concentration the residue was chromatographed over silica gel with methanol/ammonia. The product crystallized from hot acetonitrile. Yield: 3.6 g (34%) of rac-cis-4b-(2-amino-ethyl)-2-chloro-4b,5,6,7,8,8a,9,10-octahydro-phenanthren-8a-ol as white crystals; m.p. 119°–120° C.

11.5. rac-cis-4b-(2-Amino-ethyl)-2-chloro-4b,5,6,7,8,8a,9,10-octahydro-phenanthren-8a-ol (3.6 g, 0.0129 mol) was dissolved in 70 ml of ethanol. A 5N ethanolic HCl solution (10 ml, 0.05 mol) was added dropwise and the mixture was concentrated. The residue crystallized from isopropyl alcohol/ether. Yield: 3.9 g (96%) of rac-cis-4b-(2-amino-ethyl)-2-chloro-4b,8a-ol hydrochloride as white crystals; m.p. 248°–250° C.

EXAMPLE 12

12.1. 18.2 g of potassium tert-butylate (0.162 mol) were added portionwise at −78° C. to a solution of 17.2 g of 8-chloro-1,2,3,4-tetrahydro-naphthalen-1-one (0.0952 mol) in 170 ml of THF while gassing with argon. The mixture was stirred at −78° C. for 2 hrs. and then a solution of 22.5 ml of 1,4-dibromobutane (41.1 g, 190 mol) in 120 ml of THF was added dropwise. The cooling bath was removed and the mixture was stirred at RT for 62 hrs. Water was added, the mixture was extracted with ether, the organic phase was washed with a saturated aqueous sodium chloride solution, dried over MgSO4, filtered off, concentrated and the residue was chromatographed over silica gel with hexan/ether 4:1. The product crystallized from hexane at −78° C. Yield: 6.6 g (30%) of 8′-chloro-3′4′-dihydro-spiro[cyclopentan-1,2′(1′H)-naphthalen]-1′-one as white crystals; m.p. 26°–27° C.

12.2. 52.3 g of methyltriphenylphosphonium bromide/sodium amide mixture (0.126 mol) were stirred for ⅔hr. in 500 ml of THF at RT under argon. A solution of 13.4 g of 8′-chloro-3′4′-dihydro-spiro[ cyclopentane-1,2′(1′H)-naphthalen]-1′-one (0.057mol)in 130 ml of THF was added dropwise to the yellow suspension and the mixture was then stirred for 18 hrs. Water was added, the mixture was extracted with ether, the organic phase was washed with a saturated aqueous sodium chloride solution, dried over MgSO4, filtered off and concentrated. The residue was suspended in 300 ml of hot hexan, cooled to 0° C. and filtered off (the filter cake consisted of triphenylphosphine oxide). The product was concentrated and chromatographed over silica gel with hexane. Yield: 4.9 g (71%) of 8′-chloro-1′-methylene-3′4′-dihydro-spiro[cyclopentane-1,2′(1′H)-naphthalene] as a colourless liquid.

MS: m/e (% basic peak)=232 ($C_{15}H_{17}Cl^+$, 32), 217 (5), 191 (100), 175 (17), 164 (29), 141 (16), 129 (21), 115 (26). 12.3. A solution of 4.2 ml of chlorosulphonyl isocyanate (0.0481 mol) in 50 ml of ether was added dropwise at −78° C. while gassing with argon to a solution of 9.8 g of 8′-chloro-1′-methylene-3′4′-dihydro-spiro[cyclopentane-1,2′(1′H)-naphthalene](0.0404 mol) in 100 ml of ether. The mixture was stirred at −78° C. for 15 min., left to warm to RT within 1 hr. and concentrated. A by-product crystallized from ether and was filtered off under suction. The product then crystallized from the mother liquor in ether. Yield: 2.80 g (19%) of rac-cis-9-chloro-1,2,4,5-tetrahydro-3a,9b-butano-naphtho[2,1-b]furan-2-ylidene-sulphamoyl chloride [(E) or (Z) or (E/Z) mixture] as white crystals; m.p. 110°–112° C. 12.4.1.42 g (0.0374 mol) of lithium aluminium hydride were suspended in 40 ml of dioxan under argon. A solution of 2.8 g of rac-cis-9-chloro-1,2,4,5-tetrahydro-3a,9b-butano-naphtho[2,1b]furan-2-ylidene-sulphamoyl chloride [(E) or (Z) or (E/Z) mixture] (0.0748 mol) in 30 ml of THF was added dropwise and the mixture was boiled under reflux for 22 hrs. 1 ml of water, 2 ml of a 15 percent aqueous NaOH solution and 4 ml of water were cautiously added dropwise in succession at ~40° C. to form a complete white precipitate. After filtration and concentration the residue was chromatographed over silica gel with methanol/ ammonia 9:1. The product was suspended in ether, filtered off under suction, washed with ether and dried in vacuo. Yield: 1.40 g (67%) of rac-cis-4b-(2-amino-ethyl)-4-chloro-4b,5,6,7,8,8a,9,10-octahydro-phenanthren-8a-ol as white crystals; m.p. 112°–116° C.

12.5. rac-cis-4b-(2-Amino-ethyl)-4-chloro-4b,5,6,7,8,8a,9,10-octahydro-phenanthren-8a-ol (1.35 g, 0.00482 mol) was dissolved in 40 ml of ethanol. A 5N ethanolic HCl solution (1.0 ml, 0.005 mol) was added dropwise and the mixture was concentrated. The residue crystallized from acetonitrile: Yield: 1.25 g (82%) of rac-cis-4b-(2-amino-ethyl)-4-chloro-4b,5,6,7,8,8a,9,10-octahydro-phenanthren-8a-ol hydrochloride as white crystals; m.p. 248°–250° C.

EXAMPLE 13

13.1.33.8 g of potassium tert-butylate (0.301 mol) were added portionwise at −78° C. to a solution of 35.2 g of 7-chloro-5-fluoro-1,2,3,4-tetrahydro-naphthalen-1-one (0.177 mol) in 350 ml of THF while gassing with argon. The mixture was stirred at −78° C. for 2 hrs. and then a solution of 41.9 ml of 1,4-dibromobutane (76.5 g, 0.354 mol) in 200 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO4, filtered off, concentrated and the residue was chromatographed over silica gel with hexane/toluene 7:3. Yield: 18.4 g (42%) of 7′-chloro-5′-fluoro-3′4′-dihydro-spiro[cyclo-pentane-1,2′(1′H)-naphthalen]-1′-one as a yellowish liquid.

MS: m/e (% basic peak)=252 ($C_{14}H_{14}ClFO^{30}$, 19), 211 (100), 183 (14), 170 (15), 142 (22), 107 (19), 81 (16). 13.2. 36.5 g of methyltriphenylphosphonium bromide/sodium amide mixture (0.0875 mol) were stirred for ⅔hr. in 400 ml of THF at RT under argon. A solution of 18.4 g of 7′-chloro-5′-fluoro-3′4′-dihydro-spiro[cyclopentane-1,2′(1′H)-naphthalen]-1′-one (0.0729mol) in 180 ml of THF was added dropwise to the yellow suspension and the mixture was then stirred for ⅔hr. Water was added, the mixture was extracted with ether, the organic phase was washed with a lo saturated aqueous sodium chloride solution, dried over MgSO4, filtered off and concentrated. The residue was suspended in 300 ml of hot hexane, cooled to 0° C. and filtered off (the filter cake consisted of triphenylphosphine oxide). The product was concentrated and chromatographed over silica gel with hexane. Yield: 17.4 g (95%) of 7′-chloro-5′-fluoro-1′-methylene-3′4′-dihydro-spiro[cyclopentane-1,2′(1′H)-naphthalene] as a colourless liquid.

MS: m/e (% basic peak)=250 ($C_{15}H_{16}ClF^+$, 20), 209 (100), 193 (20), 74 (10), 159 (13), 146(16),133(15).

13.3. A solution of 1.9 ml of chlorosulphonyl isocyanate (0.0219 mol) in 20 ml of ether was added dropwise at −78° C. while gassing with argon to a solution of 5.0 g of 7′-chloro-5′-fluoro-1′-methylene-3′4′-dihydro-spiro[cyclopentane-1,2′(1′H)-naphthalene] (0.0199 mol) in 50 ml of ether. The mixture was stirred at −78° C. for 15 min. and left to warm to RT within 1 hr. The mixture was concentrated and the product was crystallized from ether. Yield: 2.85 g (37%) of rac-cis-8-chloro-6-fluoro-1,2,4,5-tetrahydro-3a,9b-butano-naphtho[2,1 -b]furan-2-ylidene-sulphamoyl chloride [(E) or (Z) or (E/Z) mixture] as off-white crystals; m.p. 195°–200° C.

13.4.1.3 g (0.0347 mol) of lithium aluminium hydride were suspended in 35 ml of dioxan under argon. A solution of 2.7 g of rac-cis-8-chloro-6-fluoro-1,2,4,5-tetrahydro-3a,9b-butano-naphtho-[2,1-b]furan-2-ylidene-sulphamoyl chloride [(E) or (Z) or (E/Z) mixture] (0.0069 mol) in 100 ml of THF was added dropwise and the mixture was boiled under reflux for 16 hrs. 1.3ml of water, 2.6 ml of a 15 percent aqueous NaOH solution and 3.9 ml of water were cautiously added dropwise in succession at ~40° C. to form a complete white precipitate After filtration and concentration the residue was chromatographed over silica gel with methanol/ammonia 49:1. The product crystallized from acetonitrile. Yield: 0.6 g (29%) of rac-cis-4b-(2-amino-ethyl)-3-chloro-1-fluoro-4b,5,6,7,8,8a,9,10-octahydro-phenanthren-8a-ol as white crystals; m.p. 158°–162° C.

13.5. rac-cis-4b-(2-Amino-ethyl)-3-chloro-1-fluoro-4b,5,6,7,8,8a,9,10-octahydro-phenanthrene-8a-ol (3.7 g, 0.0124 mol) was dissolved in 90 ml of ethanol. A 5N ethanolic HCl solution (2.95 ml, 0.0149 mol) was added dropwise and the mixture was concentrated. The residue crystallized from ethanol. Yield: 3.83 g (92%) of rac-cis-4b-(2-amino-ethyl)-3-chloro-1-fluoro-4b,5,6,7,8,8a,9,10-octahydro-phenanthren-8a-ol hydrochloride as white crystals; m.p. 316°–317° C.

EXAMPLE 14

14.1. 16 g of potassium tert-butylate (0.142 mol) were added portionwise at −78° C. to a solution of 18 g of 5,7-dichloro-1,2,3,4-tetrahydro-naphthalen-1-one (0.0837 mol) in 180 ml of THF while gassing with argon. The mixture was stirred at −78° C. for 2 hrs. and then a solution of 19.8 ml of 1,4-dibromobutane (36.1 g, 0.167 mol) in 100 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with hexane/ethyl acetate 9:1. Yield 7.9 g (35%) of 5'7'-dichloro-3'4'-dihydro-spiro[cyclopentane-1,2'(1'H)-naphthalen]-1'-one as a yellowish liquid.

MS: m/e (% basic peak)=268 ($C_{14}H_{14}Cl^2O^+$, 24), 227 (100), 186 (19), 158 (24), 123 (29), 81 (20).

14.2. 41.5 g of methyltriphenylphosphinium bromide/sodium amide mixture (0.0997 mol) were stirred for ¾ hr. in 410 ml of THF at RT under argon. A solution of 12.2 g of 5'7'-dichloro-3'4'-dihydro-spiro-[cyclopentane-1,2'(1'H)-naphthalen]-1'-one (0.0453mol)in 60 ml of THF was added dropwise to the yellow suspension and the mixture was then stirred for 62 hrs. Water was added, the mixture was extracted with ether, the organic phase was washed with a saturated aqueous sodium chloride solution, dried over MgSO$_4$, filtered off, concentrated and the residue was chromatographed over silica gel with hexane. Yield: 9.75 g (81%) of 5',7'-dichloro-1'-methylene-3'4'-dihydro-spiro[cyclopentane-1,2'(1'H)-naphthalene] as a colourless liquid.

MS: m/e (% basic peak)=266 ($C_{15}H_{16}Cl_2^+$, 18), 225 (100), 209 (12), 190 (13), 175 (e), 163 (10), 152 (10)

14.3. A solution of 5.84 ml of chlorosulphonyl isocyanate (0.0669 mol) in 20 ml of ether was added dropwise at −78° C. while gassing with argon to a solution of 14.9 g of 5',7'-dichloro-1'-methylene-3'4'-dihydro-spiro[cyclopentane-1,2'(1'H)-naphthalene] (0.0556 mol) in 150 ml of ether. The mixture was stirred at −78° C. for 15 min. and left to warm to RT within 1 hr. The resulting crystallizate (byproduct) was filtered off under suction and the mother liquor was crystallized in ether. Yield: 4.82 g (21%) of rac-cis-6,8-dichloro-1,2,4,5-tetrahydro-3a,9b-butano-naphtho[2,1 -b]furan-2-ylidene-sulphamoyl chloride [(E) or (Z) or (E/Z) mixture] as yellowish crystals; m.p. 180°–184° C.

1'4.4. 2.06 g (0.0543 mol) of lithium aluminium hydride were suspended in 50 ml of dioxan under argon. A solution of 4.48 g of rac-cis-6,8-dichloro-1,2,4,5-tetrahydro-3a,9b-butano-naphtho[2,1 -b]furan-2-ylidene-sulphamoyl chloride [(E) or (Z) or (E/Z) mixture] (0.011 mol) in 50 ml of THF was added dropwise and the mixture was boiled under reflux for 17 hrs. 2.1 ml of water, 2.1 ml of a 15 percent aqueous NaOH solution and 6.3 ml of water were cautiously added dropwise in succession at ~40° C. to form a complete white precipitate. After filtration and concentration the residue was chromatographed over silica gel with methanol/ammonia (99:1). The product was suspended in ether, filtered off under suction, washed with ether and dried in vacuo. Yield: 1.08 g (31%) of rac-cis-4b-(2-amino-ethyl)-1,3-dichloro-4b ,5,6,7,8,8a,9,10-octahydro-phenanthren-8a-ol as white crystals; m.p. 169°–171° C.

14.5. rac-cis-4b-(2-Amino-ethyl)-1,3-dichloro-4b,5,6,7,8,8a, 9,10-octahydro-phenanthren-8a-ol (1.11 g, 0.00353 mol) was dissolved in 30 ml of methanol. A 4.89N ethanolic HCl solution (0.72 ml, 0.00353 mol) was added dropwise and the mixture was concentrated. The residue crystallized from methanol/ether. Yield: 1.09 g (88%) of rac-cis-4b-(2-amino-ethyl)-1,3-dichloro-4b,5,6,7,8,8a,9,10-octahydro-phenanthren-8a-ol hydrochloride as white crystals; m.p. 303°–305° C.

EXAMPLE 15

15.1. 24.7 g of potassium tert-butylate (0.22 mol) were added portionwise at −78° C. to a solution of 27.9 g of 6,7-dichloro-1,2,3,4-tetrahydro-naphthalen-1-one (0.13mol) in 280ml of THF while gassing with argon. The mixture was stirred at −78° C. for 2 hrs. and then a solution of 30.7 ml of 1,4-dibromobutane (56 g, 0.26 mol) in 150 ml of THF was added dropwise. The cooling bath was removed and the mixture was stirred at RT for 16 hrs. Water was added, the mixture was extracted with ether, the organic phase o was washed with a saturated aqueous sodium chloride solution, dried over MgSO$_4$, filtered off, concentrated and the residue was chromatographed over silica gel with hexane/toluene 3:2. Yield: 17.8 g (51%) of 6'7'-dichloro-3'4'-dihydro-spiro[cyclopentane-1,2'(1'H)-naphthalen]-1'-one as a yellowish liquid.

MS: m/e (% basic peak)=268 ($C_{14}H_{14}Cl_2O^+$, 18), 227 (100), 186 (15), 158 (12), 123 (11), 81 (11).

5.2. 5.0 g of methyltriphenylphosphonium bromide/sodium amide mixture (0.012 mol) were stirred for ¾hr. in 50 ml of THF at RT under argon. A solution of 2.7 g of 6',7'-dichloro-3'4'-dihydro-spiro[cyclopentane-1,2'(1'H)-naphthalen]-1'-one (0.010mol) in 30 ml of THF was added dropwise to the yellow suspension and the mixture was then stirred for 178 hrs. Water was added, the mixture was extracted with ether, the organic phase was washed with a saturated sodium chloride solution, dried over MgSO$_4$, filtered off and concentrated. The residue was chromatographed over silica gel with hexane/CH$_2$Cl$_2$. Yield: 2.4 g (90%) of 6'7'-dichloro-1 '-methylene-3'4'-dihydro-sprio[cyclopentane-1,2'(1'H)-naphthalene] as a yellowish liquid.

MS: m/e (% basic peak)=266 ($C_{15}H_{16}Cl_2^+$, 15), 225 (100), 209 (9), 190 (9), 175 (6), 162 (7), 152 (8), 139 (6), 15.3. A solution of 0.92 ml of chlorosulphonyl isocyanate (0.0206 mol) in 10 ml of ether was added dropwise at −78° C. while gassing with argon to a solution of 2.3 g of 6'7'-dichloro-1'-methylene-3'4'-dihydro-spiro[cyclopentane-1,2'(1'H)-naphthalene (0.0088 mol) in 25 ml of ether. The mixture was stirred at −78° C. for 15 min. and left to warm to RT within 1 hr. The mixture was concentrated and the product was crystallized from ether. Yield: 1.65 g (46%) of rac-cis-7,8-dichloro-1,2,4,5-tetrahydro-3a,9b-butano-naphtho[2,1-b]furan-2-ylidene-sulphamoyl chloride [(E) or (Z) or (E/Z) mixture] as off-white crystals; m.p. 188°–190° C.

15.4. 0.74 g (0.0196 mol) of lithium aluminium hydride were suspended in 20 ml of dioxan under argon. A solution of 1.6 g of rac-cis-7,8-dichloro-1,2,4,5-tetrahydro-3a,9b-butano-naphtho[2,1  b]furan-2-ylidene-sulphamoyl chloride [(E) or (Z) or (E/Z) mixture] (0.00391 mol) in 16 ml of THF was added dropwise and the mixture was boiled under reflux for 22 hrs. 0.8 ml of water, 1.6 ml of a 15 percent aqueous NaOH solution and 1.6 ml of water were cautiously added dropwise in succession at ~40° C. to form a complete white precipitate. After filtration and concentration the residue was chromatographed over silica gel with methanol/ ammonia 49:1. The product was suspended in ether, filtered off under suction, washed with ether and dried in vacuo. Yield: 0.64 g (52%) of rac-cis-4b-(2-amino-ethyl)-2,3-dichloro-4b,5,6,7,8,8a,9,10-octahydro-phenanthren-8a-ol as white crystals; m.p. 189°–191° C.

15.5. rac-cis-4b-(2-Amino-ethyl)-2,3-dichloro-4b,5,6,7,8,8a,9,10-octahydro-phenanthren-8a-ol (2.4 g, 0.00763 mol) was dissolved in 75 ml of ethanol. A 5N ethanolic HCl solution (2 ml, 0.010 mol) was added dropwise and the mixture was concentrated. The residue crystallized from ethanol/ether. Yield: 2.3 g (86%) of rac-cis-4b-(2-amino-ethyl)-2,3-dichloro-4b,5,6,7,8,8a,9,10-octahydro-phenanthren-8a-ol hydrochloride as white crystals; m.p. 290°–295°) C.

EXAMPLE 16

16.1. 2.5 g of rac-cis-4b-(2-aminoethyl)-3-benzyloxy-4b,5,6,7,8,8a,9,10-octahydro-phenanthren-8a-ol (0.0071 mol) were dissolved in 50 ml of THF and a solution of 5.07 ml of acetyl chloride (0.071 mol) in 10 ml of THF was added dropwise at 25° C. under argon. The mixture was boiled under reflux for 1 hr., then poured into water and extracted with ether. The organic phase was dried with MgSO$_4$, filtered off, concentrated and the residue was chromatographed over silica gel with ethyl acetate. The product was recrystallized from ether. Yield: 1.56 g (56%) of rac-cis-N-[2(6-benzyloxy-10a-hydroxy-1,2,3,4,4a,9,10,10a-octahydro-phenanthren-4a-yl)-ethyl]-acetamide as white crystals; m.p. 178°–179° C.

16.2. 0.29 g (0.0077 mol) of lithium aluminium hydride were suspended in 30 ml of THF under argon. A solution of 1.5 g of rac-cis-N-[2-(6-benzyloxy-10a-hydroxy-1,2,3,4,4a,9,10,10a-octahydro-phenanthren-4a-yl)-ethyl]-acetamide (0.0038 mol) in 30 ml of THF was added dropwise thereto and the mixture was boiled under reflux for 3 hrs. 0.9 ml of a 2:1 NaOH 28%/water mixture was cautiously added dropwise at 5° C. to form a complete white precipitate. After filtration and concentration the residue was chromatographed over silica gel with acetonitrile. The product crystallized from ether. Yield: 0.98 g (68%) of rac-cis-3-benzyloxy-4b-(2-ethylamino-ethyl)-4b,5,6,7,8,8a,9,10-octahydro-phenenthren-8a-ol as white crystals; m.p.108°–110° C.

16.3. 1.63 g of rac-cis-3-benzyloxy-4b-(2-ethylamino-ethyl)-4b,5,6,7,8,8a,9,10-octahydro-phenanthren-8a-ol (0.0043 mol) were dissolved in 80 ml of THF, 0.64 ml (0.0046 mol) of triethylamine were added and a solution of 0.32 ml of acetyl chloride (0.0045 mol) in 5 ml of THF was added dropwise at 25° C. under argon. The mixture was boiled under reflux for ½ hrs., then poured into water and extracted with ether. The organic phase was dried with MgSO$_4$, filtered off, concentrated and the residue was chromatographed over silica gel with THF. Yield: 2.09 g (100%) of rac-cis-N-[2-(6-benzyloxy-10a-hydroxy-1,2,3,4,4a,9,10,10a-octahydro-phenanthren-4a-yl)ethyl]-N-ethyl-acetamide as a yellowish oil.

MS: m/e (% basic peak)=421 ($C_{27}H_{35}NO^+$, 0.6), 312 (2.4), 290 (6.6), 225 (5.6), 199 (3.6), 115 (85), 100 (29), 91 (100), 58 (56).

16.4. 0.73 g (0.019 mol) of lithium aluminium hydride was suspended in 50 ml of THF under argon. A solution of 2.0 g of rac-cis-N-[2-(6-benzyloxy-10a-hydroxy-1,2,3,4,4a,9,10,10a-octahydro-phenanthren-4a-yl)ethyl]-N-ethyl-acetamide (0.0047 mol) in 20 ml of THF was added dropwise and the mixture was boiled under reflux for 1½ hrs. 20 ml of ethyl acetate, 0.7 ml of water, 0.7 ml of a 15 percent aqueous NaOH solution and 2.1 ml of water were cautiously added dropwise in succession at RT to form a complete white precipitate. After filtration and concentration the residue was chromatographed over silica gel with THF. Yield: 1.56 g (81%) of rac-cis-3-benzyloxy-4b-(2-diethylamino-ethyl)-4b,5,6,7,8,8a,9,10-octahydro-phenanthren-8a-ol as a yellowish oil.

MS: m/e (% basic peak)=407 ($C_{27}H_{37}NO_{2+}$, 0.42), 145 (33), 86 (77), 57 (100).

16.5. 1.51 g of rac-cis-3-benzyloxy-4b-(2-diethylamino-ethyl)-4b, 5,6,7,8,8a,9,10-octahydro-phenanthren-8a-ol (0.0037mol) were dissolved in 150 ml of ethanol. After the addition of 0.15 g of 10 percent Pd—C catalyst the mixture was hydrogenated for 1 hr. at RT under 1 atm. The mixture was filtered, the filtrate was concentrated and the residue was chromatographed over silica gel with methanol. The product crystallized from ether. Yield: 0.91 g (78%) of rac-cis-4b-(2-diethylamino-ethyl)-4b,5,6,7,8,8a,9,10-octahydro-phenanthrene-3,8a-diol as white crystals; m.p. 197°–199° C.

16.6. rac-cis-4b-(2-Diethylamino-ethyl)-4b,5,6,7,8,8a,9,10-octa-hydro-phenanthren-3,8a-diol (0.96 g, 0.003 mol) was dissolved in 25 ml of methanol. A 4.89N ethanolic HCl solution (0.61 ml, 0.003 mol) was added dropwise and the mixture was concentrated. The residue crystallized from acetonitrile. Yield: 0.98 g (92%) of rac-cis-4b-(2-diethylamino-ethyl)-4b,5,6,7,8,8a,9,10-octahydro-phenanthrene-3,8a-diol hydrochloride as white crystals; m.p. 155°–157° C.

EXAMPLE 17

17.1. 1.22 g of rac-cis-3-benzyloxy-4b-(2-ethylamino-ethyl)-4b,5,6,7,8,8a,9,10-octahydro-phenanthren-8a-ol (0.003 mol) were dissolved in 100 ml of methanol. After the addition of 0.35 g of 10 percent Pd—C catalyst the mixture was hydrogenated for 2 hrs. at RT under 1 atm. The mixture was filtered, the filtrate was concentrated and the residue was chromatographed over silica gel with ethanol. After concentration a white solid was obtained. Yield: 0.80 g (86%) of rac-cis-4b-(2-ethylamino-ethyl)- 4b,5,6,7,8,8a,9,10-octahydro-phenanthrene-3,8a-diol; m.p. 189°–191° C.

17.2. rac-cis-4b-(2-Ethylamino-ethyl)-4b,5,6,7,8,8a,9,10-octahydro-phenanthrene-3,8a-diol (0.8 g, 0.0027 mol) was dissolved in 40 ml of methanol. A 4.89N ethanolic HCl solution (0.56 ml, 0.0027 mol) was added dropwise and the mixture was concentrated. The residue crystallized from ethanol/ether. Yield: 0.76 g (84%) of rac-cis-4b-(2-ethylamino-ethyl)-4b,5,6,7,8,8a,9,10-octahydro-phenanthrene-3,8a-diol hydrochloride as white crystals; m.p. 219°–221° C.

EXAMPLE 18

18.1. 2.5 g of rac-cis-4b-(2-aminoethyl)-3-benzyloxy-4b,5,6,7,8,8a,9,10-octahydro-phenanthren-8a-ol (0.0071 mol) were dissolved in 50 ml of THF and a solution of 1.24 ml of propionyl chloride (0.014 mol) in 5 ml of THF was added dropwise at 25° C. under argon. The mixture was boiled under reflux for 1 hr. The mixture was concentrated and the residue was chromatographed over silica gel with ethyl acetate. The product was recrystallized from ether. Yield: 1.75 g (60%) of rac-cis-N-[2-(6-benzyloxy-10a-hydroxy-1,2,3,4,4a,9,10,-10a-octahydro-phenanthren-4a-yl)-ethyl]-propionamide as white crystals; m.p. 154°–155° C.

18.2. 0.18 g (0.0047 mol) of lithium aluminium hydride was suspended in 30 ml of THF under argon. A solution of 0.5 g of rac-cis-N-[2-(6-benzyloxy-10a-hydroxy-1,2,3,4,4a,9,10,10a-octahydro-phenanthren-4a-yl)-ethyl]-propionamide (0.0012 mol) in 10 ml of THF was added dropwise and the mixture was boiled under reflux for 2 hrs. 0.9 ml of a 2:1 NaOH 28%/water mixture was cautiously added dropwise at 25° C. to form a complete white precipitate. After filtration and concentration the residue was chromatographed over silica gel with ethanol. The solid obtained was stirred vigourously in hexane for 15 hrs., filtered off under suction and dried in vacuo. Yield: 0.36 g (81%) of rac-cis-3-benzyloxy-4b-(2-propylamino-ethyl)- 4b,5,6,7,8,8a,9,10-octahydro-phenanthren-8a-ol as white crystals; m.p. 99°–101° C.

18.3. 1.14 g of rac-cis-3-benzyloxy-4b-(2-propylamino-ethyl)-4b,5,6,7,8,8a,9,10-octahydro-phenanthren-8a-ol (0.0029 mol) were dissolved in 100 ml of methanol. After the addition of 0.25 g of 10 percent Pd—C catalyst the mixture was hydrogenated for 1 hr. at RT under 1 atm. The mixture was filtered, the filtrate was concentrated and the residue was chromatographed over silica gel with ethanol. The product crystallized from ether. Yield: 0.66 g (75%) of rac-cis-4b-(2-propylamino-ethyl)-4b,5,6, 7,8,8a,9,10-octahydro-phenanthrene-3,8a-diol as white crystals; m.p. 185°–187° C.

18.4. rac-cis-4b-(2-Propylamino-ethyl)-4b,5,6,7,8,8a,9,10-octahydro-phenanthrene-3,8a-diol (0.66 g, 0.0021 mol) was dissolved in 30 ml of methanol. A 4.89N ethanolic HCl solution (0.44 ml, 0.0021 mol) was added dropwise and the mixture was concentrated. The residue crystallized from acetonitrile. Yield: 0.58 g (78%) of rac-cis-4b-(2-propylamino-ethyl)-4b,5,6,7,8,8a,9,10-octahydro-phenanthrene-3,8a-diol hydrochloride as white crystals; m.p. 182°–184° C.

EXAMPLE 19

19.1. 2.5 g of rac-cis-4b-(2-aminoethyl)-3-benzyloxy-4b,5,6,7,8,8a,9,10-octahydro-phenanthren-8a-ol (0.0071 mol) were dissolved in 50 ml of THF and a solution of 1.3 ml of cyclopropane-carboxylic acid chloride (0.0142 mol) in 5 ml of THF was added dropwise at 25o(:; under argon. The mixture was boiled under reflux for 1 hr., then poured into water and extracted with ether. The organic phase was dried with MgSO$_4$, filtered off, concentrated and the residue was chromatographed over silica gel with ethyl acetate. After concentration a white solid was obtained. Yield: 2.0 g (67%) of rac-cis-N-[2-(6-benzyloxy-10a-hydroxy-1,2,3,4,4a,9,10,10a-octahydro-phenanthren-4a-yl)-ethyl]-cyclopropanecarboxamide; m.p. 176°–178° C.

19.2. 0.67 g (0.0178 mol) of lithium aluminium hydride was suspended in 120 ml of THF under argon. A solution of 1.87 g of rac-cis-N-[2-(6-benzyloxy-10a-hydroxy-1,2,3,4,4a,9,10,10a-octahydro-phenanthren-4a-yl)-ethyl]-cyclopropanecarboxamide (0.0044 mol) in 30 ml of THF was added dropwise and the mixture was boiled under reflux for 1½ hrs. 3.6 ml of a 2:1 NaOH 28%/water mixture was cautiously added dropwise at room temperature to form a complete white precipitate. After filtration and concentration the residue was chromatographed over silica gel with ethanol. The product crystallized from hot hexane. Yield: 1.85 g (100%) of rac-cis-3-benzyloxy-4b-(2-cyclopropylmethylamino-ethyl)-4b,5,6,7,8,8a, 9,10-octahydro-phenanthren-8a-ol as a yellowish oil.

MS: m/e (% basic peak)=405 (C$_{27}$H$_{35}$NO$_2^+$, 6.2), 349 (1.3), 296 (6.1) 290 (6.6), 217 (17), 199 (13), 98 (22), 91 (100), 84 (65), 55 (38).

19.3. 1.73 g of rac-cis-3-benzyloxy-4b-(2-cyclopropyl-methyl-amino-ethyl)-4b ,5,6,7,8,8a,9,10-octahydro-phenanthren-8a-ol (0.0042 mol) were dissolved in 40 ml of methanol. After the addition of 0.46 g of 10 percent Pd—C catalyst the mixture was hydrogenated for 1 hr. at RT under 1 atm. The mixture was filtered, the filtrate was concentrated and the residue was chromatographed over silica gel with ethanol. The product crystallized from ether. Yield: 0.59 g (44%) of rac-cis-4b-(2-cyclopropylmethylamino-ethyl)-4b,5,6,7,8,8a,9,10-octahydro-phenanthrene-3,8a-diol as white crystals; m.p. 167°–169° C.

19.4. rac-cis-4b-(2-Cyclopropylmethylamino-ethyl)-4b,5,6,7,8,8a,9,10-octahydro-phenanthrene-3,8a-diol (1 g, 0.003 mol) was dissolved in 40 ml of methanol. A 4.89N ethanolic HCl solution (0.65 ml, 0.003 mol) was added dropwise and the mixture was concentrated. The residue crystallized from ether. Yield: 1.02 g (91%) of rac-cis-4b-(2-cyclopropylmethylamino-ethyl)-4b,5,6,7, 8,8a,9,10-octahydro-phenanthrene-3,8a-diol hydrochloride as white crystals; m.p. 207°–209° C.

EXAMPLE 20

20.1. 3.0 g of rac-cis-4b-(2-aminoethyl)-3-benzyloxy-4b,5,6,7,8,8a,9,10-octahydro-phenanthren-8a-ol (0.0085 mol) were dissolved in 50 ml of THF, 1.3 ml (0.0094 mol) of triethylamine were added and a solution of 1.13 g of cyclobutanecarboxylic acid chloride (0.0094 mol) in 5 ml of THF was added dropwise at 25° C. under argon. The mixture was boiled under reflux for 1 hr., then poured into water and extracted with CH$_2$Cl$_2$. The organic phase was dried with MgSO$_4$, filtered off, concentrated and the residue was chromatographed over silica gel with ethyl acetate. There was obtained a crystalline material which was suspended in ether, then filtered off under suction and dried in vacuo. Yield: 3.15 g (85%) of rac-cis-N-[2-[6-benzyloxy-10a-hydroxy-1,2,3,4,4a,9,10,10a-octahydro-phenanthren-4a-yl)-ethyl]-cyclobutanecarboxamide as white crystals; m.p. 111°–113° C.

EXAMPLE 20

20.2. 1.08 g (0.0286 mol) of lithium aluminium hydride were suspended in 120 ml of THF under argon. A solution of 3.1 g of rac-cis-N-[2-[6-benzyloxy-10a-hydroxy-1,2,3,4,4a,9,10,10a,-phenanthren- 4a-yl)-ethyl]-cyclobutanecarboxamide (0.0071 mol) in 20 mi of THF was added dropwise and the mixture was boiled under reflux for 1½ hrs. 5.9 ml of a 2:1 NaOH 48% water mixture was cautiously added dropwise at 10° C. to form a complete white precipitate. After filtration and concentration the residue was chromatographed over silica gel with acetonitrile. The product was distilled in a bulb-tube. Yield: 3.16 g (100%) of rac-cis-3-benzyloxy-4b-(2-cyclobutylmethylamino-ethyl)-4b,5,6,7,8,8a,9,10-octahydro-phenanthren-8a-ol as a yellowish oil; b.p. 250° C./0.04 Torr.

MS: m/e (% basic peak)=419 ($C_{28}H_{37}NO_2^+$, 7.4), 363 (1.9), 346 (6.3), 308 (6.5), 290 (9), 217 (23), 199 (15), 157 (5.5), 112 (24), 98 (56) 91 (100).

20.3.3.1 g of rac-cis-3-benzyloxy-4b-(2-cyclobutylmethylamino-ethyl)-4b,5,6,7,8,8a,9,10-octahydro-phenanthren-8a-ol (0.0074 mol) were dissolved in 100 ml of ethanol. After the addition of 0.4 g of 10 percent Pd—C catalyst the mixture was hydrogenated for 1 hr. at RT under 1 atm. The mixture was filtered, the filtrate was concentrated and the residue was chromatographed over silica gel with ethanol. The product crystallized from ether. Yield: 1.56 g (69%) of rac-cis-4b-(2-cyclobutylmethylamino-ethyl)-4b,5,6,7,8,8a,9,10-octahydro-phenanthrene-3,8a-diol as white crystals; m.p. 140°–142° C.

0.4. rac-cis-4b-(2-Cyclobutylmethylamino-ethyl)-4b,5,6,7,8,8a, 9,10-octahydro-phenanthrene-3,8a-diol (1.52 g, 0.0046 mol) was dissolved in 50 ml of methanol. A 4.89N ethanolic HCl solution (0.94 ml, 0.0046 mol) was added dropwise and the mixture was concentrated. The residue crystallized from ethanol/ether. Yield: 1.62 g (96%) of rac-cis-4b-(2-cyclobutylmethylamino-ethyl)-4b,5,6,7,8,8a,9,10-octahydro-phenanthrene-3,8a-diol hydrochloride as white crystals; m.p. 210°–21 2° C.

EXAMPLE 21

21.1.2.0 g of rac-cis-4b-(2-aminoethyl)-3-benzyloxy-4b,5,6,7,8,8a,9,10-octahydro-phenanthren-8a-ol (0.0057 mol) were dissolved in 50 ml of THF and a solution of 1.5 ml of phenylacetyl chloride (0.0113 mol) in 5 ml of THF was added dropwise at 25° C. under argon. The mixture was boiled under reflux for ½ hrs. The 1½ mixture was concentrated and the residue was chromatographed over silica gel with $CH_2Cl_2$/ethyl acetate 1:1. The product was suspended in ether, filtered off and dried in vacuo. Yield: 1.5 g (56%) of rac-cis-N-[2-(6-benzyloxy-10a-hydroxy-1,2,3,4,4a,9,10,10a-octahydro-phenanthren-4a-yl)-ethyl]-phenylacetamide as white crystals; m.p. 114°–116° C.

21.2. 0.5 g (0.0013 mol) of lithium aluminium hydride were suspended in 40 ml of THF under argon. A solution of 1.55 g of rac-cis-N-[2-(6-benzyloxy-10a-hydroxy-1,2,3,4,4a,9,10,10a-octahydro-phenanthren-4a-yl)-ethyl]-phenylacetamide (0.0033 mol) in 15 ml of THF was added dropwise and the mixture was boiled under reflux for 1½ hrs. 1.8 ml of a 2:1 NaOH 28%/water mixture was cautiously added dropwise at RT to form a complete white precipitate. After filtration and concentration the residue was chromatographed over silica gel with ethanol. Yield: 0.66 g (44%) of s rac-cis-3-benzyloxy-4b-(2-phenethylamino-ethyl)-4b,5,6,7,8,8a,9,10-octahydro-phenanthren-8a-ol as a yellowish oil.

MS: m/e (% basic peak)=445 ($C_{31}H_{37}NO_2^+$, 1.75), 364 (26), 346 (48), 289 (11), 134 (13), 105 (24), 91 (100), 58 (19), 44 (20).

21.3.0.66 g of rac-cis-3-benzyloxy-4b-(2-phenethylamino-ethyl)-4b,5,6,7,8,8a,9,10-octahydro-phenanthren-8a-ol (0.0014 mol) was dissolved in 60 ml of ethanol. After the addition of 0.16 g of 10 percent Pd—C catalyst the mixture was hydrogenated for 1½ hrs. at RT under 1 atm. The mixture was filtered, the filtrate was concentrated and the residue was chromatographed over silica gel with ethanol. The product crystallized from hexane. Yield: 0.29 g (56%) of rac-cis-4b-(2-phenethylamino-ethyl)-4b,5,6,7,8,8a,9,10-octahydro-phenanthrene-3,8a-diol a-8a-diol as white crystals; m.p. 82°–84° C.

21.4. rac-cis-4b-(2-Phenethylamino-ethyl)-4b,5,6,7,8,8a,9,10-octahydro-phenanthrene-8a-diol (0.15 g, 0.004 mol) was dissolved in 10 ml of methanol. A 4.89N ethanolic HCl solution (0.084 ml, 0.0004 mol) was added dropwise and the mixture was concentrated. The residue crystallized from ether. Yield: 0.16 g (100%) of rac-cis-4b-(2-phenethylamino-ethyl)-4b,5,6,7,8,8a,9,10-octahydro-phenanthrene-8a-diol hydrochloride as white crystals; m.p. 160°–162° C.

EXAMPLE 22

22.1.5.5 g of rac-cis-4b-(2-aminoethyl)-3-methoxy-4b,5,6,7,8,8a,9,10-octahydro-phenanthren-8a-ol (0.020 mol) were dissolved in 40 ml of $CH_2Cl_2$, 3.35 ml of triethylamine (0.024 mol) were added and 1.7 ml of acetyl chloride (0.024 mol) were added dropwise at 0° C. under argon. The mixture was boiled under reflux for 1 hr., then poured into water and extracted with ether. The organic phase was dried with $MgSO_4$, filtered off, concentrated and the residue was chromatographed over silica gel with $CH_2Cl_2$/methanol 10:1. The product was recrystallized from ether. Yield: 2.7 g (43%) of rac-cis-N-[2-(10a-hydroxy-6-methoxy-1,2,3,4,4a,9,10,-10a-octahydro-phenanthren-4a-yl)-ethyl]-acetamide as white crystals.

MS: m/e (% basic peak)=317 ($C_{19}H_{27}NO_3^+$, 2.4), 299 (3.4), 240 (8), 213 (68), 171 (15), 121 (18), 87 (100).

22.2 3.16 g (0.084 mol) of lithium aluminium hydride were suspended in 60 ml of dioxan under argon. A solution of 5.3 g of rac-cis-N-[2-(10a-hydroxy-6-methoxy-1,2,3,4,4a,9,10,10a-octahydro-phenanthren-4a-yl)-ethyl]-acetamide (0.017 mol) in 60 ml of THF was added dropwise and the mixture was boiled under reflux for 20 hrs. 3.2 ml of water, 3.5 ml of a 15 percent aqueous NaOH solution and 3.2 ml of water were cautiously added dropwise in succession at RT to form a complete white precipitate. After filtration and concentration the residue was chromatographed over silica gel with $CH_2Cl_2$/methanol 10:1. The product crystallized from hot hexane. Yield: 5.0 g (98%) of rac-cis-4b-(2-ethylamino-ethyl)-3-methoxy-4b,5,6,7,8,8a,9,10-octahydro-phenanthren-8a-ol as white crystals.

MS: m/e (% basic peak)=303 ($C_{19}H_{29}NO_2^+$, 13), 232 (39), 214 (16), 171 (6), 121 (5), 58 (100).

22.3. rac-cis-4b-(2-Ethylamino-ethyl)-3-methoxy-4b,5,6,7,8,8a,9,10-octahydro-phenanthren-8a-ol (5.0 g, 0.016 mol) was dissolved in 50 ml of ether. HCl gas was introduced and the mixture was concentrated. The residue crystallized from ether. Yield: 5.0 g (88%) of rac-cis-4b-(2-ethylamino-ethyl)-3-methoxy-4b,5,6,7,8,8a,9,10-octahydro-phenanthren-8a-ol hydrochloride as white crystals; m.p. 217°–21 9° C.

EXAMPLE 23

3.1.8.2 g of rac-cis-4b-(2-aminoethyl)-3-methoxy-4b,5,6,7,8,8a,9,10-octahydro-phenanthren-8a-ol (0.0298 mol) were dissolved in 60 ml of THF, 5 ml of triethylamine (0.0357 mol) were added and 3.1 ml of cyclopropanecarboxylic acid chloride (0.0357 mol) were added dropwise at 25° C. under argon. The mixture was boiled under reflux for 1 hr., then poured into water, extracted with ether and washed with 1N aqueous HCl solution. The organic phase was dried with $MgSO_4$, filtered off and concentrated. Yield: 10 g (97%) of rac-cis-N-[2-(10a-hydroxy-6-methoxy-1,2,3,4,4a,9,10,10a-octahydro-phenanthren-4a-yl)-ethyl]-cyclopropanecarboxamide as a crude material.

MS: m/e (% basic peak)=343 ($C_{21}H_{29}NO_3^+$, 2.6), 325 (4.3), 255 (16), 240 (14), 213 (100), 171 (41), 121 (31), 113 (100), 98 (76), 69(79). 23.2.1.1 g (0.029 mol) of lithium aluminium hydride were suspended in 20 ml of THF under argon. A solution of 2.0 g of rac-cis-N-[2-(10a-hydroxy-6-methoxy-1,2,3,4,4a,9,10,10a-octahydrophenanthren-4a-yl)-ethyl]-cyclopropanecarboxamide (0.006 mol) in 20 ml of THF was added dropwise and the mixture was boiled under reflux for 20 hrs. 1.1 ml of water, 1.5 ml of a 15 percent aqueous NaOH solution and 1.1 ml of water were cautiously added dropwise in succession at RT to form a complete white precipitate. After filtration and concentration the residue was chromatographed over silica gel with ethanol. The product crystallized from hot hexane. Yield: 1.4 g (73%) of rac-cis-4b-(2-cyclopropylmethylamino-ethyl)-3-methoxy-4b,5,6,7,8,8a, 9,10-octahydro-phenanthren-8a-ol as white crystals.

MS: m/e (% basic peak)=329 ($C_{21}H_{31}NO_2^+$, 24), 232 (65), 214 (37), 171 (12), 121 (13), 99 (17), 84 (100), 55 (58).

23.3. rac-cis-4b-(2-Cyclopropylmethylamino-ethyl)-3-methoxy-4b,5,6,7,8,8a,9,10-octahydro-phenanthren-8a-ol (6.4 g, 0.019mol) was dissolved in 70 ml of ether. HCl gas was introduced and the mixture was concentrated. The residue crystallized from $CH_2Cl_2$/ ether. Yield: 4.6 g (54%) of rac-cis-4b-(2-cyclopropylmethylamino-ethyl)-3-methoxy-4b,5,6,7,8,8a,9,10-octahydro-phenanthren-8a-ol hydrochloride as white crystals; m.p. 180°–182° C.

EXAMPLE 24

24.1.4.0 g of rac-cis-4b-(2-aminoethyl)-3-methoxy-4b,5,6,7,8,8a,9,10-octahydro-phenanthren-8a-ol (0.0145 mol) were dissolved in 30 ml of $CH_2Cl_2$. 2.4 ml of triethylamine (0.0174 mol) were added and 1.8 ml of cyclobutanecarboxylic acid chloride (0.0174 mol) were added dropwise at 0° C. under argon. The mixture was stirred at RT for 20 hrs., then poured into water, extracted with ether and washed with a 1N aqueous HCl solution. The organic phase was dried with $MgSO_4$, filtered off, concentrated and the residue was chromatographed over silica gel with $CH_2Cl_2$/methanol 10:1. Yield: 3.7 g (70%) of rac-cis-N-[2-(10a-hydroxy-6-methoxy-1,2,3,4,4a,9,1 0, 10a-octahydro-phenanthren-4a-yl)-ethyl]-cyclobutanecarboxamide as an oil.

MS: m/e (% basic peak)=357 ($C_{22}H_{31}NO_3^+$, 4.9), 339 (2.6), 240 (14), 214 (30), 171 (11), 159 (9), 127 (100), 72 (48), 56 (61).

24.2.3.45 g (0.091 mol) of lithium aluminium hydride were suspended in 70 ml of dioxan under argon. A solution of 6.5 g of rac-cis-N-[2-(10a-hydroxy-6-methoxy-1,2,3; 4,4a,9,10,10a-octa-hydro-phenanthren-4a-yl)-ethyl]-cyclobutanecarboxamide (0.018 mol) in 80 ml of THF was added dropwise and the mixture was boiled under reflux for 20 hrs. 3.5 ml of water, 4.5 ml of a 15 percent aqueous NaOH solution and 3.5 ml of water were cautiously added dropwise in succession at RT to form a complete white precipitate. The mixture was filtered and the filtrate was concentrated. Yield: 6.2 g (98%) of rac-cis-4b-(2-cyclobutylmethyl-amino-ethyl)-3-methoxy-4b,5,6,7,8,8a,9,10-octahydro-phenanthren-8a-ol as a crude colourless oil.

MS: m/e (% basic peak)=343 ($C_{22}H_{33}NO_2^+$, 33), 270 (17), 232 (81), 214 (40), 171 (16), 159 (12), 147 (9), 121 (17), 98 (100).

24.3. rac-cis-4b-(2-Cyclobutylmethylamino-ethyl)-3-methoxy-4b,5,6,7,8,8a,9,10-octahydro-phenanthren-8a-ol (6.2 g, 0.018mol) was dissolved in 100 ml of ether. HCl gas was introduced and the mixture was concentrated. The residue crystallized from $CH_2Cl_2$/ ether. Yield: 5.7 g (83%) of rac-cis-4b-(2-cyclobutylmethylamino-ethyl)-3-methoxy-4b,5,6,7,8,8a,9,10-octahydro-phenanthren-8a-ol hydrochloride as white crystals; m.p. 156°–158° C.

EXAMPLE 25

25.1.2.2 g of rac-cis-4b-(2-aminoethyl)-4b,5,6,7,8,8a,9,10-octa-hydro-phenanthren-8a-ol (0.009 mol) were dissolved in 10 ml of a 85 percent aqueous formic acid solution. 3 ml of a 37 percent aqueous formaldehyde solution were added and the mixture was boiled under reflux for 16 hrs. The mixture was cooled to RT, poured into 50 ml of water, made basic with 50 ml of 4N NaOH, extracted with $CH_2Cl_2$, the organic phase was washed with a saturated aqueous sodium chloride solution, dried over $MgSO_4$, filtered off, concentrated and chromatographed over silica gel with ethyl acetate/methanol 1:4. Yield: 1.23 g (50%) of rac-cis-4b-(2-dimethylamino-ethyl)-4b,5,6,7,8,8a,9,10-octahydro-phenanthren-8a-ol as a yellowish viscous oil.

MS: m/e (% basic peak)=273 ($C_{18}H_{27}NO^{30}$, 5.0), 217 (2.3), 184 (2.3), 129 (2.9), 128 (2.9), 91 (2.3), 72 (4), 58 (100).

25.2. rac-cis-4b-(2-Dimethylamino-ethyl)-4b,5,6,7,8,8a,9,10-octa-hydro-phenanthren-8a-ol (1.2 g, 0.00439 mol) was dissolved in 30 ml of ethyl acetate. A 4.8N ethanolic HCl solution (1.05 ml, 4.83 mol) was added dropwise, whereby the product crystallized out. Yield: 1.17 g (86%) of rac-cis-4b-(2-dimethylamino-ethyl)-4b,5,6,7,8,8a,9,10-octahydro-phenanthren-8a-ol hydrochloride as white crystals; m.p. 161°–164° C.

EXAMPLE 26

26.1.10 g of rac-cis-4b-(2-aminoethyl)-3-fluoro-4b,5,6,7,8,8a,9,10-octahydro-phenanthren-8a-ol (0.038 mol) were dissolved in 28 ml of a 85 percent aqueous formic acid solution. 5.6 ml of a 37 percent aqueous formaldehyde solution were added and the mixture was boiled under reflux for 16 hrs. The mixture was cooled to RT, poured into 50 ml of water, made basic with 2N NaOH, extracted with $CH_2Cl_2$, the organic phase was washed with a saturated aqueous sodium chloride solution, dried over $MgSO_4$, filtered off, concentrated and chromatographed over silica gel with $CH_2Cl_2$/methanol/ammonia 90:9:1. Yield: 2.34 g (49%) of rac-cis-4b-(2-dimethylamino-ethyl)-3-fluoro-4b,5,6,7,8,8a,9,10-octahydro-phenanthren-8a-ol as a yellowish oil.

MS: m/e (% basic peak)=291 ($C_{18}H_{26}FNO^+$, 2.3), 235 (0.4), 159 (1.9), 146 (1.4), 133 (1.55), 72 (4), 58 (100).

26.2. rac-cis-4b-(2-Dimethylamino-ethyl)-3-fluoro-4b,5,6,7,8,8a,9,10-octahydro-phenanthren-8a-ol (2.81 g, 0.0096 mol) was dissolved in 50 ml of ethanol. A 4.89N ethanolic HCl solution (1.96 ml, 0.0096 mol) was added dropwise and the mixture was concentrated. The residue crystallized from ether. Yield: 2.73 g (86%) of rac-cis-4b-(2-dimethylamino-ethyl)-3-fluoro-4b,5,6,7,8,8a,9,10-octahydro-phenanthren-8a-ol hydrocloride as white crystals; m.p. 194°14 196° C.

EXAMPLE 27

27.1.6.9 g of rac-cis-4b-(2-aminoethyl)-3-chloro-4b,5,6,7,8,8a,9,10-octahydro-phenanthren-8a-ol (0.024 mol) were dissolved in 18.1 ml of a 85 percent aqueous formic acid solution. 3.63 ml of a 37 percent aqueous formaldehyde solution were added and the mixture was boiled under reflux for 16 hrs. The mixture was cooled to RT, poured into 50 ml of water, made basic with 2N NaOH, extracted with CH$_2$Cl$_2$, the organic phase was washed with a saturated aqueous sodium chloride solution, dried over MgSO$_4$, filtered off, concentrated and chromatographed over silica gel with CH$_2$Cl$_2$/methanol 10:1. The product was distilled in a bulb-tube. Yield: 4.41 g (58%) of rac-cis-3-chloro-4b-(2-dimethylamino-ethyl)-4b,5,6,7,8,8a,9,10-octahydro-phenanthren-8a-ol as a colourless oil (58%); b.p. 220°-230° C/0.01 Torr.

MS: m/e (% basic peak)=307 (C$_{18}$H$_{26}$ClNO$^+$, 2.3), 251 (0.75), 128 (1.1), 115 (1), 72 (4.5), 58 (100).

27.2. rac-cis-3-chloro-4b-(2-dimethylamino-ethyl)-4b,5,6,7,8,8a,9,10-octahydro-phenanthren-8a-ol (3.56 g, 0.011 mol) was dissolved in 60 ml of methanol. A 4.89N ethanolic HCl solution (2.36 ml, 0.011 mol) was added dropwise and the mixture was concentrated. The residue crystallized from ethanol/ether. Yield: 3.43 g (86%) of rac-cis-3-chloro-4b-(2-dimethylamino-ethyl)-4b,5,6,7,8,8a,9,10-octahydro-phenanthren-8a-ol hydrochloride as white crystals; m.p. 240°-242° C.

EXAMPLE 28

28.1. 2.0 g of rac-cis-4b-(2-amino-ethyl)-3-benzyloxy-4b,5,6,7,8,8a,9,10-octahydro-phenanthren-8a-ol (0.0057 mol) were dissolved in 40 ml of ethanol. After the addition of 0.4 g of 10 percent Pd—C catalyst the mixture was hydrogenated for 1 hr. at RT under 1 atm. The mixture was filtered and the filtrate was concentrated. The product crystallized from acetonitrile. Yield: 1.31 g (88.5%) of rac-cis-4b-(2-amino-ethyl)-4b,5,6,7,8,8a,9,10-octahydro-phenanthrene-3,8a-diol as white crystals; m.p. 141°-143° C. (dec.).

28.2. rac-cis-4b-(2-Amino-ethyl)-4b,5,6,7,8,8a,9,10-octahydro-phenanthrene-3,8a-diol (1.76 g, 0.0067 mol) was dissolved in 30 ml of THF. A 4.89N ethanolic HCl solution (1.38 ml, 0.0067 mol) was added dropwise and the mixture was concentrated. The residue crystallized from THF/ether. Yield: 1.74 g (87%) of rac-cis-4b-(2-amino-ethyl)-4b,5,6,7,8,8a,9,10-octahydro-phenanthrene-3,8a-diol hydrochloride as white crystals; m.p. 130°-132° C.

EXAMPLE 29

29.1. A mixture of 1.39 g of rac-cis-4b-(2-amino-ethyl)-4b,5,6,7,8,8a,9,10-octahydro-phenanthrene-3,8a-diol (0.00531 mol), 1.22 ml of 2-bromopyridine (1.98 g, 0.0125 mol), 1.05 g of potassium carbonate (0.0076 mol) and 125 mg of copper powder (0.00197 mol) was boiled under reflux for 48 hours in 100 ml of pyridine. After concentration the residue was chromatographed over silica gel with methanol/ammonia 19:1. The product was recrystallized in acetonitrile. Yield: 0.77 g (43%) of rac-cis-4b-(2-amino-ethyl)-3-(pyridin-2-yloxy)-4b,5,6,7,8,8a,9,10-octahydro-phenanthren-8a-ol as beige crystals; m.p. 157°-159° C.

29.2. rac-cis-4b-(2-Amino-ethyl)-3-(pyridin-2-yloxy)-4b,5,6,7,8,8a,9,10-octahydro-phenanthren-8a-ol (1.09 g, 0.00322 mol) was dissolved in 20 ml of methanol. A 4.89N ethanolic HCl solution (0.66 mi, 0.00323 mol) was added dropwise and the mixture was concentrated. The residue crystallized from ethanol/ether. Yield: 1.04 g (86%) of rac-cis-4b-(2-amino-ethyl)-3-(pyridin-2-yloxy)-4b,5,6,7,8,8a,9,10-octahydro-phenanthren-8a-ol hydrochloride as white crystals; m.p. 170°-172° C.

EXAMPLE 30

30.1. 1.8 g of rac-cis-4b-(2-amino-ethyl)-3-(pyridin-2-yloxy)-4b,5,6,7,8,8a,9,10-octahydro-phenanthren-8a-ol (0.00532 mol) were dissolved in 6 ml of a 85 percent aqueous formic acid solution. 1.8 ml of a 37 percent aqueous formaldehyde solution were added and the mixture was boiled under reflux for ½ hrs. The mixture was cooled to RT, poured into 50 ml of water, made basic with 27 ml of 4N NaOH, extracted with CH$_2$Cl$_2$, the organic phase was washed with a saturated aqueous sodium chloride solution, dried over MgSO$_4$, filtered off, concentrated and chromatographed over silica gel with methanol. Yield: 1.6 g (82%) of rac-cis-4b-(2-dimethylamino-ethyl)-3-(pyridin-2-yloxy)-4b,5,6,7,8,8a,9,10-octahydro-phenanthren-8a-ol as a yellowish oil.

MS: m/e (% basic peak)=366 (C$_{23}$H$_{30}$N$_2$O$_2$$^+$, 3.9), 295 (3.7), 278 (7.2), (2.2), 72 (6.5), 58 (100).

30.2. rac-cis-4b-(2-Dimethylamino-ethyl)-3-(pyridin-2-yloxy)-4b,5,6,7,8,8a,9,10-octahydro-phenanthren-8a-ol (1.6 g, 0.00437 mol) was dissolved in 30 ml of ethyl acetate. A 4.78N ethanolic HCl solution (1.0 ml, 0.00478 mol) was added dropwise, whereby the product crystallized out. Yield: 1.62 g (92%) of rac-cis-4b-(2-dimethylamino-ethyl)-3-(pyridin-2-yloxy)-4b,5,6,7,8,8a,9,10-octahydro-phenanthren-8a-ol hydrochloride as white crystals; m.p. 209°-210° C.

EXAMPLE 31

31.1. 1 g of rac-cis-4b-(2-aminoethyl)-3-benzyloxy-4b,5,6,7,8,8a,9,10-octahydro-phenanthren-8a-ol (0.00284 mol) was dissolved in 2 ml of a 85 percent aqueous formic acid solution. 0.4 ml of a 37 percent aqueous formaldehyde solution was added and the mixture was boiled under reflux for 4 hrs. The mixture was cooled to RT, poured into 20 ml of water, made basic with 2N NaOH, extracted with ether, the organic phase was washed with water, dried over Na$_2$SO$_4$, filtered off, concentrated and chromatographed over silica gel with methanol and methanol/ammonia 9:1. Yield: 0.74 g (69%) of rac-cis-3-benzyloxy-4b-(2-dimethylamino-ethyl)-4b,5,6,7,8,8a,9,10-octahydro-phenanthren-8a-ol as a pale yellow oil.

MS: m/e (% basic peak)=379 (C$_{25}$H$_{33}$NO$_2$$^+$, 7.4), 308 (5.8), 288 (4.5) 217 (9), 91 (25), 58 (100)

31.2. 2.75 g of rac-cis-3-benzyloxy-4b-(2-dimethylamino-ethyl)-4b,5,6,7,8,8a,9,10-octahydro-phenanthren-8a-ol (0.0072 mol) were dissolved in 80 ml of THF, 2.2 mi of triethylamine (0,015 mol) were added and a solution of 1.1 ml of acetyl chloride (0,015 mol) in 5 ml of THF was added dropwise at 25° C. under argon. The mixture was boiled under reflux for 2 hrs., then poured into water and extracted with CH$_2$Cl$_2$. The organic phase was dried with MgSO$_4$, filtered off, concentrated and the residue was chromatographed over silica gel with methanol. Yield: 2 g (66%) of acetic acid rac-cis-3-benzyloxy-4b-(2-dimethylamino-ethyl)-4b,5,6,7,8,8a,9,10-octahydro-phenanthren-8a-yl ester as a yellowish oil.

MS: m/e (% basic peak)=421 (C$_{27}$H$_{35}$NO$_3$$^+$, 0.9), 362 (1.4), 290 (3), 270 (2.8e), 199 (7.1), 91 (26), 58 (100).

1.3. 2.34 g of acetic acid rac-cis-3-benzyloxy-4b-(2-diethyl-amino-ethyl)-4b,5,6,7,8,8a,9,10-octahydro-phenanthren-8a-yl ester (0.0055 mol) were dissolved in 20 ml of methanol. After the addition of 0.23 g of 10 percent Pd—C catalyst the mixture was hydrogenated for 2 hrs. at RT under 1 atm. The mixture was filtered, the filtrate was concentrated and the residue was chromatographed over silica gel with methanol/ammonia 19:1. The product crystallized from ether. Yield: 1.84 g (90%) of acetic acid rac-cis-4b-(2-dimethylamino-ethyl)-3-hydroxy-4b,5,6,7,8, 8a,9,10-octahydro-phenanthren-8a-yl ester as white crystals; m.p. 229°–230° C.

31.4. Acetic acid rac-cis-4b-(2-dimethylamino-ethyl)-3-hydroxy-4b,5,6,7,8,8a,9,10-octahydro-phenanthren-8a-yl ester (0.95 g, 0.0029 mol) was dissolved in 50 ml of methanol. A 4.89N ethanolic HCl solution (0.6 ml, 0.0029 mol) was added dropwise and the mixture was concentrated. The residue crystallized from ether. Yield: 0.97 g (91%) of acetic acid rac-cis-4b-(2-dimethylamino-ethyl)-3-hydroxy-4b,5,6,7,8,8a,9,10-octahydro-phenanthren-8a-yl ester hydrochloride as white crystals; m.p. 222°–224° C.

EXAMPLE 32

32.1. 0.6 g of rac-cis-3-benzyloxy-4b-(2-dimethylamino-ethyl)-4b,5,6,7,8,8a,9,10-octahydro-phenanthren-8a-ol (0.00158 mol) was dissolved in 20 ml of methanol. After the addition of 0.1 g of 10 percent Pd—C catalyst the mixture was hydrogenated for 1 hr. at RT under 1 atm. The mixture was filtered, the filtrate was concentrated and the residue was chromatographed over silica gel with methanol. The product crystallized from ether. Yield: 0.33 g (72%) of rac-cis-4b-(2-dimethylamino-ethyl)-4b,5,6,7,8,8a,9,10-octahydro-phenanthrene-3,8a-diol as white crystals; m.p. 189°–90° C.

2.2. rac-cis-4b-(2-Dimethylamino-ethyl)-4b,5,6,7,8,8a,9,10-octahydro-phenanthrene-3,8a-diol (2.2 g, 0.0076 mol) was dissolved in 100 ml of methanol. A 4.89N ethanolic HCl solution (1.55 ml, 0.076 mol) was added dropwise and the mixture was concentrated. The residue crystallized from methanol/ether. Yield: 2.4 g (97%) of rac-cis-4b-(2-dimethylamino-ethyl)-4b,5,6,7,8,8a,9,10-octahydro-phenanthrene-3,8a-diol hydrochloride as white crystals; m.p. 222°–224° C.

EXAMPLE 33

33.1. 1.4 g of rac-cis-3-benzyloxy-4b-(2-dimethylamino-ethyl)-4b,5,6,7,8,8a,9,10-octahydro-phenanthren-8a-ol (0.0037 mol) were dissolved in 20 ml of THF, 1.11 ml of triethylamine (0.0079 mol) were added and a solution of 0.86 ml of butyryl chloride (0.0082 mol) in 5 ml of THF was added dropwise at 25° C. under argon. The mixture was boiled under reflux for 3 hrs., then poured into water and extracted with $CH_2Cl_2$. The organic phase was dried with $MgSO_4$, filtered off and concentrated. Yield: 1.59 g (96%) of butyric acid rac-cis-3-benzyloxy-4b-(2-dimethylamino-ethyl)-4b,5,6,7,8,8a,9,10-octahydro-phenanthren-8a-yl ester as a brown oil.

MS: m/e (% basic peak)=449 ($C_{29}H_{39}NO_3^+$, 1.2), 362 (3.1), 334 (1.5), 290 (6.6), 270 (4.9), 199 (9.5), 149 (3), 141 (4.5), 91 (39), 73 (13 ), 58 (100).

33.2. 1.59 g of butyric acid rac-cis-3-benzyloxy-4b-(2-dimethyl-amino-ethyl)-4b,5,6,7,8,8a,9,10-octahydro-phenanthren-8a-yl ester (0.0035 mol) were dissolved in 20 ml of methanol. After the addition of 0.16 g of 10 percent Pd—C catalyst the mixture was hydrogenated for 1.5 hrs. at RT under 1 atm. The mixture was filtered, the filtrate was concentrated and the residue was chromatographed over silica gel with MeOH. The product crystallized from ether. Yield: 0.87 g (70%) of butyric acid rac-cis-4b-(2-dimethylamino-ethyl)-3-hydroxy-4b,5,6,7,8,8a,9,10-octahydro-phenanthren-8a-yl ester as white crystals; m.p. 158°–160° C.

3.3. Butyric acid rac-cis-4b-(2-dimethylamino-ethyl)-3-hydroxy-4b,5,6,7,8,8a,9,10-octahydro-phenanthren-8a-yl ester (0.9 g, 0.0025 mol) was dissolved in 30 ml of methanol. A 4.89N ethanolic HCl solution (0.51 ml, 0.0025 mol) was added dropwise and the mixture was concentrated. The residue crystallized from acetonitrile/ether. Yield: 0.92 g (95%) of butyric acid rac-cis-4b-(2-dimethylamino-ethyl)-3-hydroxy-4b,5,6,7,8,8a,9,10-octahydro-phenanthren-8a-yl ester hydrochloride as white crystals; m.p. 210°–212° C.

EXAMPLE 34

34.1. 2.0 g of rac-cis-4b-(2-aminoethyl)-3-methoxy-4b,5,6,7,8,8a,9, 10-octahydro-phenanthren-8a-ol (0.0072 mol) were dissolved in 5.1 ml of an 85 percent aqueous formic acid solution. 1 ml of a 37 percent aqueous formaldehyde solution was added and the mixture was boiled under reflux for 16 hrs. The mixture was cooled to RT, poured into 5 ml of water, made basic with 8 ml of 2N NaOH, extracted with ethyl acetate, the organic phase was washed with a saturated aqueous sodium chloride solution, dried over $MgSO_4$, filtered off, concentrated and chromatographed over silica gel with ethyl acetate/methanol/ammonia 90:9:1. Yield: 0.99 g (45%) of rac-cis-4b-(2-dimethylamino-ethyl)-3-methoxy-4b,5,6,7,8,8a,9,10-octahydro-phenanthren-8a-ol as a yellowish oil.

MS: m/e (% basic peak)=303 ($C_{19}H_{29}NO_2^+$, 4), 232 (9), 214 (3.5), 58 (100 )

34.2. rac-cis-4b-(2-Dimethylamino-ethyl)-3-methoxy-4b,5,6,7,8,8a,9,10-octahydro-phenanthren-8a-ol (0.99 g, 0.0032 mol) was dissolved in 10 ml of ethanol. A 4.89N ethanolic HCl solution (0.67 ml, 0.0032 mol) was added dropwise and the mixture was concentrated. The residue crystallized from acetonitrile/ether. Yield: 0.9 g (82%) of rac-cis-4b-(2-dimethylamino-ethyl)-3-methoxy-4b,5,6,7,8,8a,9,10-octahydro-phenanthren-8a-ol hydrochloride as white crystals; m.p. 159°–161° C.

EXAMPLE 35

35.1. 4.5 g of rac-cis-4b-(2-aminoethyl)-2,3-dichloro-4b,5,6,7,8,8a,9,10-octahydro-phenanthren-8a-ol (0.0143 mol) were dissolved in 16 ml of an 85 percent aqueous formic acid solution. 3.0 ml of a 37 percent aqueous formaldehyde solution were added and the mixture was boiled under reflux for 19 hrs. The mixture was cooled to RT, poured into 100 ml of water, made basic with 120 ml of 4N NaOH, extracted with $CH_2Cl_2$, the organic phase was washed with a saturated aqueous sodium chloride solution, dried over $MgSO_4$, filtered off, concentrated and chromatographed over silica gel with isopropyl alcohol/ethyl acetate 3:1. Yield: 1.5 g (31%) of rac-cis-2,3-dichloro-4b-(2-dimethylamino-ethyl)-4b,5,6,7,8,8a,9,10-octahydro-phenanthren-8a-ol as a yellowish oil.

MS: m/e (% basic peak)=341 ($C_{18}H_2Cl_2NO^+$, 1.0), 117 (5.3), 72 (4), 58 (100 )

35.2. rac-cis-2,3-Dichloro-4b-(2-dimethylamino-ethyl)-4b,5,6,7,8,8a,9,10-octahydro-phenanthren-8a-ol (1.5 g, 0.00438 mol) was dissolved in 30 ml of ethanol. A 5N ethanolic HCl solution (1.0 ml, 0.005 mol) was added dropwise and the mixture was concentrated. The residue crystallized from isopropyl alcohol/ether. Yield: 1.22 g (74%) of rac-cis-2,3-dichloro-4b-(2-dimethylamino-ethyl)-4b,5,6,7,8,8a,9,10-octahydro-phenanthren-8a-ol hydrochloride as white crystals; m.p. 211°–215° C.

EXAMPLE 36

36.1. 2.34 g of rac-cis-4b-(2-dimethylamino-ethyl)-3-fluoro-4b,5,6,7,8,8a,9,10-octahydro-phenanthren-8a-ol (0.008 mol) were dissolved in 50 ml of THF, 5 ml of triethylamine (0.036 mol) were added and a solution of 2.5 ml of acetyl chloride (0.035 mol) in 5 ml of THF was added dropwise at 25° C. under argon. The mixture was boiled under reflux for 4 hrs., then poured into water and extracted with $CH_2Cl_2$. The organic phase was dried with $MgSO_4$, filtered off, concentrated and the residue was chromatographed over silica gel with methanol. Yield: 1.69 g (63%) of acetic acid rac-cis-4b-(2-dimethylamino-ethyl)-3-fluoro-4b,5,6,7,8,8a,9,10-octahydro-phenanthren-8a-yl ester as a yellowish oil.

MS: m/e (% basic peak)=333 ($C_{20}H_{28}FNO_2^+$, 0.25), 274 (2.3), 202 (1.4), 159 (3.2), 146 (1.6), 133 (1.65), 109 (1.05), 73 (5), 71 (4) 58 (100).

36.2. Acetic acid rac-cis-4b-(2-dimethylamino-ethyl)-3-fluoro-5,6,7,8,8a,9,10-octahydro-phenanthren-8a-yl ester (1.69 g, 0.005 mol) was dissolved in 40 ml of ethanol. A 4.89N ethanolic HCl solution (1.03 ml, 0.005 mol) was added dropwise and the mixture was concentrated. The residue crystallized from ether. Yield: 1.25 g (67%) of acetic acid rac-cis-4b-(2-dimethylamino-ethyl)-3-fluoro-4b,5,6,7,8,8a,9,10-octahydro-phenanthren-8a-yl ester hydrochloride as white crystals; m.p. 203°–205° C.

EXAMPLE 37

37.1. 2.5 g of rac-cis-3-chloro-4b-(2-dimethylamino-ethyl)-4b,5,6,7,8,8a,9,10-octahydro-phenanthren-8a-ol (0.008 mol) were dissolved in 50 ml of THF, 5 ml of triethylamine (0.035 mol) were added and a solution of 2.5 ml of acetyl chloride (0.035 mol) in 10 ml of THF was added dropwise at 25° C. under argon. The mixture was boiled under reflux for 2 hrs., then poured into water and extracted with ethyl acetate. The organic phase was dried with $MgSO_4$, filtered off, concentrated and the residue was chromatographed over silica gel with methanol. Yield: 1.62 g (57%) of acetic acid rac-cis-3-chloro-4b-(2-dimethylamino-ethyl)-4b,5,6,7,8,8a,9,10-octahydro-phenanthren-8a-yl ester as a yellowish oil.

MS: m/e (% basic peak)=349 ($C_2H_{28}ClNO_2^+$, 0.35), 290 (2.8), 218 (2.1), 175 (2.2), 149 (3.5), 97 (6), 85 (7), 83 (8), 71 (16)

37.2. Acetic acid rac-cis-3-chloro-4b-(2-dimethylamino-ethyl)-4b,5,6,7,8,8a,9,10-octahydro-phenanthren-8a-yl ester (1.76 g, 0.005 mol) was dissolved in 30 ml of ethanol. A 4.89N ethanolic HCl solution (1.02 ml, 0.005 mol) was added dropwise and the mixture was concentrated. The residue crystallized from ether. Yield: 1.57 g (81%) of acetic acid rac-cis-3-chloro-4b-(2-dimethylamino-ethyl)-4b ,5,6,7,8,8a,9,10-octahydro-phenanthren-8a-yl ester hydrochloride as white crystals; m.p. 192°–194° C.

EXAMPLE 38

38.1. 2.0 g of rac-cis-3-chloro-4b-(2-dimethylamino-ethyl)-4b,5,6,7,8,8a,9,10-octahydro-phenanthren-8a-ol (0.0065 mol) were dissolved in 50 ml of THF, 2 ml of triethylamine (0.014 mol) were added and a solution of 1.5 ml of butyryl chloride (0.014 mol) in 5 ml of THF was added dropwise at 25° C. under argon. The mixture was boiled under reflux for 3 hrs., then poured into water and extracted with ethyl acetate. The organic phase was dried with $MgSO_4$, filtered off, concentrated and the residue was chromatographed over silica gel with methanol. Yield: 2.02 g (82%) of butyric acid rac-cis-3-chloro-4b-(2-dimethylamino-ethyl)-4b,5,6,7,8,8a,9,10-octahydro-phenanthren-8a-yl ester as a yellowish oil.

MS: m/e (% basic peak)=377 ($C_{22}H_{32}ClN_2^+$, 0.3), 290 (3.7), 218 (1.5), 183 (1.4), 73 (7.5), 71 (6.5), 58 (100).

38.2. Butyric acid rac-cis-3-chloro-4b-(2-dimethylamino-ethyl)-4b,5,6,7,8,8a,9,10-octahydro-phenanthren-8a-yl ester (2.47 g, 0.0065 tool) was dissolved in 40 ml of ethanol. A 4.89N ethanolic HCl solution (1.33 ml, 0.0065 mol) was added dropwise and the mixture was concentrated. The residue crystallized from ether. Yield: 2.2 g (82%) of butyric acid rac-cis-3-chloro-4b-(2-dimethylamino-ethyl)-4b,5,6,7,8,8a,9,10-octahydro-phenanthren-8a-yl ester hydrochloride as white crystals; m.p. 164°–166° C.

EXAMPLE 39

39.1. 12 g of rac-cis-4b-(2-amino-ethyl)-3-benzyloxy-4b,5,6,7,8,8a,9,10-octahydro-phenanthren-8a-ol (0.0341 mol) in 500 ml of acetone were added to a suspension of 7.14 g of (-)-2,2'-(1,1'-binaphthyl)-phosphoric acid (0.0205 mol)-in 900 ml of acetone. After heating at reflux there was obtained a colourless solution which crystallized at room temperature. After three further recrystallizations from methanol/isopropyl alcohol 1:1 there were obtained 4.74 g of white crystals, m.p. 29320 –295° C.

These crystals were dissolved in 200 ml of water, the solution was made basic with an aqueous 28 percent sodium hydroxide solution, filtered, extracted with $CH_2Cl_2$, the organic phase was washed with water, dried over $Na_2SO_4$, filtered off and concentrated. The residue crystallized from acetonitrile/ether. Yield: 1.67 g (14%) of (+)-cis-4b-(2-amino-ethyl)-3-benzyloxy-4b,5,6,7,8,8a,9,10-octahydro-phenanthren-8a-ol as white crystals; m.p. 124°–125° C. and $[\alpha]_D^{20}=+13.5°$ ($CHCl_3$, c=1%)

39.2. 1.57 g of (+)-cis-4b-(2-amino-ethyl)-3-benzyloxy-4b,5,6,7,8,8a,9,10-octahydro-phenanthren-8a-ol (0.00446 mol) were dissolved in 60 ml of ethanol. After the addition of 0.35 g of 10 percent Pd—C catalyst the mixture was hydrogenated for 1 hr. at RT under 1 atm. The mixture was filtered and the filtrate was concentrated. The product crystallized from acetonitrile. Yield: 1.0 g (86%) of (+)-cis-4b-(2-amino-ethyl)-4b,5,6,7,8,8a,9,10-octahydro-phenanthrene-3,8a-diol as white crystals; m.p. 186°–188° C. and $[\alpha]_D^{20}=+38.4°$ (MeOH, c=1%).

39.3. (+)-cis-4b-(2-Amino-ethyl)-4b,5,6,7,8,8a,9,10-octahydro-phenanthrene-3,8a-diol (0.96 g, 0.0037 mol) was dissolved in 30 ml of methanol. A 4.89N ethanolic HCl solution (0.75 ml, 0.0037 mol) was added dropwise and the mixture was concentrated. The residue crystallized from ether. Yield: 1.07 g (98%) of (+)-cis-4b-(2-amino-ethyl)-4b,5,6,7,8,8a,9,10-octahydro-phenanthrene-3,8a-diol hydrochloride as white crystals; m.p. 109°–111° C. $[\alpha]_D^{20}=-16.7°$ (MeOH, c=1%).

EXAMPLE 40

40.1. 6.18 g of rac-cis-4b-(2-amino-ethyl)-3-benzyloxy-4b,5,6,7,8,8a,9,-10-octahydro-phenanthren-8a-ol (0.0176 mol) in 250ml of acetone were added to a suspension of 3.68 g of (+)-2,2'-(1,1'-binaphthyl)-phosphoric acid (0.0106 mol) in 460 ml of acetone. After heating at reflux there was obtained a colourless solution which crystallized at room temperature. After three further recrystallizations from methanol/isopropyl alcohol 1:1 there were obtained 5.29 g of white crystals, m.p. 291°–293° C.

These crystals were dissolved in 300 ml of water, the solution was made basic with an aqueous 28 percent sodium hydroxide solution, filtered, extracted with CH$_2$Cl$_2$, the organic phase was washed with water, dried over Na$_2$SO$_4$, filtered off and concentrated. After chromatographed over silica gel with methanol the residue was crystallized from acetonitrile/ether. Yield: 2.63 g (42%) of (-)-cis-4b-(2-amino-ethyl)-3-benzyloxy-4b,5,6,7,8,8a,9,10-octahydro-phenanthren-8a-ol as white crystals; -m.p. 124°–125° C. and $[\alpha]_D^{20} = +11.9°$ (CHCl$_3$, c=1%).

40.2.2.94 g of (−)-cis-4b-(2-amino-ethyl)-3-benzyloxy-4b,5,6,7,8,8a,9,10-octahydro-phenanthren-Sa-ol (0.00758 tool) were dissolved in 100 ml of methanol. After the addition of 0.7 g of 10 percent Pd—C catalyst the mixture was hydrogenated for 1 hr. at RT under 1 atm. The mixture was filtered and the filtrate was concentrated. The product crystallized from acetonitrile. Yield: 1.67 g (84%) of (−)-cis-4b-(2-amino-ethyl)-4b,5,6,7,8,8a,9,10-octahydro-phenanthrene-3,Sa-diol as white crystals (84%); m.p. 185°–187° C. and $[\alpha]_D^{20} = -37.6°$ (MeOH, c=1%).

40.3. (−)-cis-4b-(2-Amino-ethyl)-4b,5,6,7,8,8a,9,10-octahydro-phenanthrene-3,8a-diol (1.84 g, 0.007 mol) was dissolved in 20 mi of methanol. A 4.89N ethanolic HCl solution (1.44 ml, 0.007 mol) was added dropwise and the mixture was concentrated. The residue crystallized from ether. Yield: 1.93 g (92%) of (−)-cis-4b-(2-amino-ethyl)-4b,5,6,7,8,8a,9,10-octahydro-phenanthrene-3,8a-diol hydrochloride as white crystals; m.p. 115°–117° C. $[\alpha]_D^{20} = -17.6°$ (MeOH, c=1%).

EXAMPLE 41

41.1.14 ml of a sulphuric acid/nitric acid 65% 1:1 mixture was slowly added dropwise to a solution of 20 g of 3'4'-dihydro-spiro[cyclopentane-1,2'(1'H)-naphthalen]-1'-one in 60 ml of sulphuric acid. After stirring for 2 hrs. at RT the mixture was poured on to 200 g of ice, extracted with ether, washed with a saturated aqueous NaHCO$_3$ solution and with water, dried on Na$_2$SO$_4$, filtered, concentrated and chromatographed over silica gel with cyclohexane/ethyl acetate 9:1. Yield: 12.7 g (52%). A sample was recrystallized from hot isopropyl ether and gave 7'-nitro-3'4'-dihydro-spiro[cyclopentane-1,2'(1'H)-naphthalen]-1'-one as white crystals; m.p. 69°–70° C.

41.2.7.04 g of 7'-nitro-3'4'-dihydro-spiro[cyclopentane-1,2'(1'H)-naphthalen]-1'-one (0.0287 mol) were dissolved in 100 ml of THF. After the addition of 1 g of 10 percent Pd—C catalyst the mixture was hydrogenated for ¾hr. at RT under 1 atm. The mixture was filtered, the filtrate was concentrated and the residue was chromatographed over silica gel with CH$_2$Cl$_2$. The product crystallized from n-hexane. Yield: 4.95 g (80%) of 7'-amino-3'4'-dihydro-spiro[cyclopentane-1,2'(1'H)-naphthalen]-1'-one as beige crystals; m.p. 78°–80° C.

41.3. 100 ml of a 1.6N solution of methyllithium in hexane (0.16 mol) were added at 0° C. to a solution of 8.28 g of 7'-amino-3'4'-dihydro-spiro[cyclopentane-1,2'(1'H)-naphthalen]-1'-one (0.0385 mol) in 100 ml of dry ether and the mixture was stirred for 2 hrs. at RT. The suspension was poured on to 200 g of ice, extracted with ether, washed with water, dried with Na$_2$SO$_4$, filtered, concentrated and chromatographed over silica gel with ether. The product was recrystallized from isopropyl ether. Yield: 4.47 g (50%) of (RS)-7'-amino-1'-methyl-3'4'-dihydro-spiro-[cyclopentane-1,2'(1'H)-naphthalen]-1'-ol as beige crystals; m.p. 119°–120° C.

41.4. A solution of 4.27 g of (RS)-7'-amino-1'-methyl-3'4'-dihydro-spiro[cyclopentane-1,2'(1'H)-naphthalen]-1'-ol (0.0185mol) and 0.47 g of iodine (0.00185 mol) in 150 ml of toluene was boiled under reflux for 1/4 hr. The mixture was cooled, washed with water, dried with Na2SO4, filtered, concentrated and chromatographed over silica gel with CH$_2$Cl$_2$. The product was distilled through a 10 cm Vigreux column. Yield: 2.51 g of 1'-methylene-3'4'-dihydro-spiro[cyclopentane-1,2'(1 'H)-naphthalene]-7'-amine as a colourless oil; b.p. 113°–115° C./0.08 Torr.

41.5.3.6 ml of benzoyl chloride (4.35 g, 0.0309 mol) were added while cooling with ice to a solution of 6.0 g of 1'-methylene-3'4'-dihydro-spiro[cyclopentane-1,2'(1 'H)-naphthalene]-7'-amine (0.0281 mol) and 4.2 ml of triethylamine (3.13 g, 0.0309 mol) in 150 ml of toluene in 100 ml of THF and the mixture was then boiled under reflux for 2 hrs. 100 ml of water were poured into the cooled solution. The mixture was extracted with ether, washed with water, dried with Na$_2$SO$_4$, filtered, concentrated and chromatographed over silica gel with CH$_2$Cl$_2$. The solid obtained was stirred vigorously in ether for 2 hrs., filtered off under suction and dried in vacuo. Yield: 6.98 g (78%) of N-[1'-methylene-3'4'-dihydro-spiro[cyclopentane-1,2'(1 'H)-naphthalene]-7'-yl]-benzamide as a white solid; m.p. 160°–161° C.

41.6. A solution of 2.3 ml of chlorosulphonyl isocyanate (3.73 g, 0.0264 mol) in 5 ml of THF was added dropwise at −78° C. while gassing with argon to a solution of 6.98 g of N-[1'-methylene-3'4'-dihydro-spiro[cyclopentane-1,2'(1 'H)-naphthalene]-7'-yl]-benzamide (0.022 mol) in 70 ml of THF. The mixture was stirred at −78° C. for 15 min. and left to warm to RT within 1 hr. The solution was concentrated after 36 hrs. Yield: 17.9 g of rac-cis-8-benzamido-1,2,4,5-tetrahydro-3a,9b-butano-naphtho[2,1 -b]furan-2-ylidene-sulphamoyl chloride [(E) or (Z) or (E/Z) mixture] as a yellow oil which was used directly in the next step. A sample was recrystallized from ethyl acetate/hexane and gave white crystals; m.p. 185°–187° C.

41.7.6.8 g (0.18 mol) of lithium aluminium hydride were suspended in 250 ml of dioxan under argon. A solution of 17.9 g of crude rac-cis-8-benzamido-1,2,4,5-tetrahydro-3a,9b-butano-naphtho[2,1b]furan-2-ylidene-sulphamoyl chloride [(E) or (Z) or (E/Z) mixture] (0.022 mol) in 250 ml of THF was added dropwise and the mixture was boiled under reflux for 24 hrs. 70 ml of ethyl acetate, 7 ml of water, 7 ml of 15 percent aqueous NaOH solution and 21 ml of water were cautiously added dropwise in succession at ∼40° C. to form a complete white precipitate. After filtration and concentration the residue was chromatographed over silica gel with methanol and methanol/ammonia 9:1. The product was suspended in ether, filtered off under suction, washed with ether and dried in vacuo. Yield: 2.58 g (33%) of rac-cis-4b-(2-amino-ethyl)-3-benzylamino-4b,5,6,7,8,8a,9,10-octahydrophenanthren-8a-ol as white crystals; m.p. 152°–154° C.

41.8.3.0 g of rac-cis-4b-(2-amino-ethyl)-3-benzylamino-4b,5,6,7,8,8a,9,10-octahydrophenanthren-8a-ol (0.00856mol) were dissolved in 300 ml of ethanol. After the addition of 1.5 g of 10 percent Pd—C catalyst the mixture was hydrogenated for 20 hrs. at RT under 50 bar. The mixture was filtered, the filtrate was concentrated and the residue was chromatographed over silica gel with methanol/ammonia 9:1. The product was recrystallized from ethanol/ether. Yield: 1.5 g of rac-cis-3-amino-4b-(2-amino-ethyl)-4b,5,6,7,8,8a,9,10-octahydro-phenanthren-8a-ol as white crystals; m.p. 160°–162° C.

41.9. rac-cis-3-Amino-4b-(2-amino-ethyl)-4b,5,6,7,8,8a,9,10-octahydro-phenanthren-8a-ol (1.5 g, 0.00576 mol) was dissolved in 30 ml of ethanol. A 4.89N ethanolic HCl solution (1.18 ml, 5.77 mol) was added dropwise thereto, the mixture was filtered over Norit and concentrated. The residue was shaken vigorously in ether for 48 hrs., filtered off under suction and dried in vacuo. Yield: 1.32 g (77%) of rac-cis-3-amino-4b-(2-amino-ethyl)-4b,5,6,7,8,8a,9,10-octahydro-phenanthren-8a-ol hydrochloride as a beige, amorphous solid; m.p. 105°–107° C.

EXAMPLE 42

42.1. A solution of 9.37 g of rac-cis-4b-(2-amino-ethyl)-3-chloro-4b,5,6,7,8,8a,9,10-octahydro-phenanthren-8a-ol (0.0304mol)in 100 ml of acetone was added to a suspension of 7.0 g of (+)-2,2'-(1,1'-binaphthyl)-phosphoric acid (0.0201 mol) in 500 ml of acetone. After slight warming there was obtained a pale yellow solution which was concentrated.

The amorphous residue was dissolved in 1 l of hot ethyl acetate, decanted and crystallized at room temperature. After three further recrystallizations from ethanol there were obtained 4.01 g of white crystals; m.p. 166°–168° C.

The crystals were dissolved in 150 ml of water, the solution was made basic with an aqueous 2N sodium hydroxide solution, filtered, extracted with CH$_2$Cl$_2$, the organic phase was washed with water, dried over Na$_2$SO$_4$, filtered off and concentrated. Yield: 1.86 g (20%) of (−)-cis-3-chloro-4b-[2-(dimethylamino-ethyl)-4b,5,6,7,8,8a,9,10-octahydro-phenanthren-8a-ol as a pale yellow oil with $[\alpha]_D^{20}=-15.2°$ (MeOH, c=1%).

42.2. (−)-cis-3-chloro-4b-(2-dimethylamino-ethyl)-4b,5,6,7,8,8a, 9,10-octahydro-phenanthren-8a-ol (1.78 g, 0.0058mol) was dissolved in 50 ml of ethanol. A 4.89N ethanolic HCl solution (1.18 ml, 0.0058 mol) was added dropwise and the mixture was concentrated. The residue crystallized from ethanol/ether. Yield: 1.67 g (84%) of (+)-cis-3-chloro-4b-(2-dimethylamino-ethyl)-4b,5,6,7,8,8a,9,10-octahydro-phenanthren-8a-ol hydrochloride as white crystals; m.p. 225°–227° C. $[\alpha]_D^{20}=+2.8°$ (MeOH, c=1%).

EXAMPLE 43

43.1.10.4 g of rac-cis-4b-(2-amino-ethyl)-3-chloro-4b,5,6,7,8,8a,9,10-octahydro-phenanthren-8a-ol (0.0337 mol) in 100 ml of acetone were added to a suspension of 7.74 g of (−)-2,2'-(1,1'-binaphthyl)-phosphoric acid (0.0222 mol) in 550 ml of acetone. After slight warming there was obtained a pale yellow solution which was concentrated.

The amorphous residue (18.8 g) was dissolved in 560 ml of hot ethyl acetate, decanted and crystallized at room temperature. After three further recrystallizations from ethanol there were obtained 5.01 g of white crystals; m.p. 166°–168° C. These crystals were dissolved in 200 ml of water, the solution was made basic with an aqueous 2N sodium hydroxide solution, filtered, extracted with CH$_2$Cl$_2$, the organic phase was washed with water, dried over Na$_2$SO$_4$, filtered off and concentrated. Yield: 2.3 g (22%) of (+)-cis-3-chloro-4b-(2-dimethylamino-ethyl)-4b,5,6,7,8,8a,9,10-octahydro-phenanthren-8a-ol as a pale yellow oil with $[\alpha]_D^{20}=+16.2°$ (MeOH, c-1%).

43.2. (+)-cis-3-chloro-4b-(2-dimethylamino-ethyl)-4b,5,6,7,8,8a,8a,9,10-octahydro-phenanthren-8a-ol (2.22 g, 0.007 mol) was dissolved in 50 ml of ethanol. A 4.89N ethanolic HCl solution (1.47 ml, 0.007 mol) was added dropwise and the mixture was concentrated. The residue crystallized from ethanol/ether. Yield: 2.11 g (85%) of (−)-cis-3-chloro-4b-(2-dimethylamino-ethyl)-4b,5,6,7,8,8a,9,10-octahydro-phenanthren-8a-ol hydrochloride as white crystals; m.p. 225°–226° C. $[\alpha]_D^{20}=+2.8°$ (MeOH, c=1%).

EXAMPLE 44

44.1. 76.7 g of potassium tert-butylate (0.68 mol) were added portionwise at −78° C. to a solution of 50 g of 1,2,3,4-tetrahydro-napthalen-1-one (0.34 mol) in 700 ml of THF while gassing with argon. The mixture was stirred at −78° C. for 2 hrs. and then a solution of 70 ml of 1,4-dibromobutane (128 g, 0.59 mol) in 150 ml of THF was added dropwise. The cooling bath was removed and the mixture was stirred at RT for 16 hrs. Water was added, the mixture was extracted with ether, the organic phase was washed with a saturated aqueous sodium chloride solution, dried over MgSO$_4$, filtered off, concentrated and the residue was chromatographed over silica gel with hexane/toluene 2:1. The product was distilled through a 20 cm Vigreux column. Yield: 29.6 g (76%) of 3'4'-dihydro-spiro[cyclopentane-1,2'(1'H)-naphthalen]-1'-one as a colourless liquid; b.p. 92°–94° C./0.08 Torr.

44.2. 134 g of methyltriphenylphosphonium bromide/sodium amide mixture (0.32 mol) were stirred for ⅔hr. in 700 ml of THF at RT under argon. A solution of 29.5 g of 3'4'-dihydro-spiro[cyclopentane-1,2'(1'H)-naphthalen]-1'-one (0.147 mol) in 200 ml of THF was added dropwise to the yellow suspension and the mixture was then stirred for 18 hrs. Water was added, the mixture was extracted with ether, the organic phase was washed with a saturated aqueous sodium chloride solution, dried over MgSO$_4$, filtered off, concentrated and the residue was chromatographed over silica gel with toluene. The product was distilled through a 20 cm Vigreux column. Yield: 26.6 g (91%) of 1'-methylene-3'4'-dihydro-spiro[cyclopentane-1,2'(1'H)-naphthalene] as a colourless liquid; b.p. 78°–79° C./0.09 Torr.

4.3. A solution of 11.6 ml of chlorosulphonyl isocyanate (0.133 mol) in 30 ml of ether was added dropwise at −78° C. while gassing with argon to a solution of 22 g of 1'-methylene-3'4'-dihydro-spiro[cyclopentane-1,2'(1'H)-naphthalene] (0.111 mol) in 200 ml of ether. The mixture was stirred at −78° C. for 15 min. and left to warm to RT within 1 hr. The resulting crystallizate was filtered off under suction, washed with ether and dried in vacuo. Yield: 31.7 g (84%) of rac-cis-1,2,4,5-tetrahydro-3a,9b-butano-naphtho[2,1-b]furan-2-ylidene-sulphamoyl chloride [(E) or (Z) or (E/Z) mixture] as yellowish crystals; m.p. 141°–144° C.

44.4. 18.4 g (0.48 mol) of lithium aluminium hydride were suspended in 500 ml of dioxan under argon. A solution of 32.9 g of rac-cis-1,2,4,5-tetrahydro-3a,9b-butano-naphtho[2,1 -b]furan-2-ylidene-sulphamoyl chloride [(E) or (Z) or (E/Z) mixture] (0.097 mol) in 300 ml of THF was added dropwise and the mixture was boiled under reflux for ½ hrs. 60 ml of a 2:1 NaOH 28%/water mixture were cautiously added dropwise at RT to form a complete white precipitate. After filtration and concentration the residue was chromatographed over silica gel with methanol. The product crystallized from acetonitrile. Yield: 9.9 g (42%) of rac-cis-4b-(2-amino-ethyl) 4b,5,6,7,8,8a,9,10-octahydro-phenanthren-8a-ol white crystals; m.p. 157°–158° C.

44.5.5 g (0.024 mol) of rac-cis-4b-(2-amino-ethyl)-4b,5,6,7,8,8a,9,10-octahydro-phenanthren-8a-ol were dissolved in 100 ml of methanol. 4.9 ml (0,024 mol) of a 4.89 N ethanolic HCl solution was then added dropwise and the mixture was concentrated. The residue crystallized from ether. Yield: 5.71 g (84%) of rac-cis-4b-(2-amino-ethyl)-4b ,5,6,7,8,8a, 9,10-octahydro-phenanthren-8a-ol hydrochloride as white crystals; m.p. 222°–224° C.

We claim:

1. A compound of the formula:

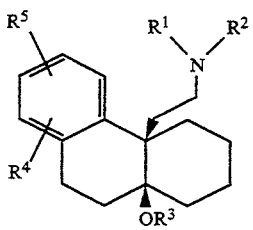

wherein $R^1$ and $R^2$ each individually are hydrogen or lower alkyl optionally substituted by aryl or $C_{3-6}$-cycloalkyl;

$R^4$ and $R^5$ are both hydrogen or are both halogen or one is hydrogen and the other is halogen, hydroxy, lower alkoxy, aryloxy or amino; and $R^3$ is hydrogen or, where no primary or secondary amino group is present, hydrogen or alkanoyl;

and pharmaceutically acceptable acid addition salts; with the proviso that all the groups $R^1$ through $R^5$ cannot simultaneously be hydrogen.

2. A compound of the formula:

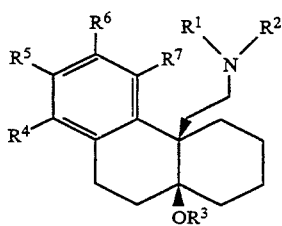

wherein:

$R^1$ and $R^2$ independently are hydrogen or lower alkyl optionally substituted by $C_{3-6}$-cycloalkyl, $R^3$ is hydrogen or, where $R^1$ and $R^2$ are both lower alkyl, $R^3$ is hydrogen or alkanoyl, and two of the groups $R^4$, $R^5$, $R^6$, and $R^7$ are halogen and the remaining two groups are hydrogen, or three of the groups $R^4$, $R^5$, $R^6$, and $R^7$ are hydrogen and the other is halogen, heteroaryloxy, lower alkoxy or hydroxy.

3. The compound of claim 2 wherein $R^1$ and $R^2$ are both hydrogen or are both lower alkyl, $R^3$ is hydrogen or, where $R^1$ and $R^2$ are both lower alkyl, $R^3$ is hydrogen or alkanoyl, and two of the groups $R^4$, $R^5$, $R^6$, and $R^7$ are halogen and the remaining two groups are hydrogen, or three of the groups $R^4$, $R^5$, $R^6$, and $R^7$ are hydrogen and the remaining group is halogen, lower alkoxy or hydroxy.

4. The compound of claim 3 wherein said compound is rac-cis-4b-(2-dimethylamino-ethyl)-3-methoxy-4b,5,6,7,8,8a,9,10-octahydro-phenanthren-8a-ol.

5. The compound of claim 3 wherein said compound is rac-cis-4b-(2-amino-ethyl)-3-chloro-1-fluoro-4b,5,6,7,8, 8a,9,10-octahydro-phenanthren-8a-ol.

6. The compound of claim 2 wherein $R^1$ and $R^2$ are lower alkyl, $R^3$ is hydrogen or alkanoyl, and all of the groups $R^4$, and $R^5$, $R^6$ and $R^7$ are hydrogen, or three of the groups $R^4$, $R^5$, $R^6$ and $R^7$ are hydrogen and the remaining group is halogen or hydroxy.

7. The compound of claim 6 having the formula:

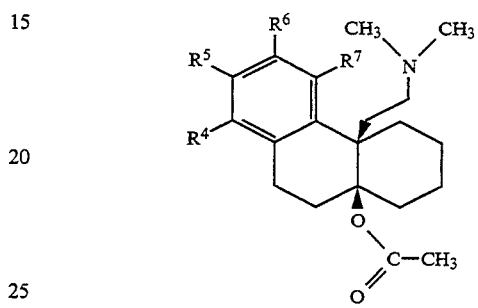

wherein all of the groups $R^4$, and $R^5$, $R^6$ and $R^7$ are hydrogen, or three of the groups $R^4$, $R^5$, $R^6$ and $R^7$ are hydrogen and the remaining group is halogen or hydroxy.

8. The compound of claim 7 wherein $R^4$, $R^5$, and $R^7$ are hydrogen and $R^6$ is halogen or hydroxy.

9. The compound of claim 8 wherein said compound is acetic acid rac-cis-4b-(2-dimethylamino-ethyl)-3-fluoro-4b,5,6,7,8,8a,9,10-octahydro-phenanthren-8a-yl ester.

10. The compound of claim 8 wherein said compound is acetic acid rac-cis-3-chloro-4b-(2-dimethylamino-ethyl)-4b,5,6,7,8,8a,9,10-octahydro-phenanthren-8a-yl ester.

11. The compound of claim 6 having the formula:

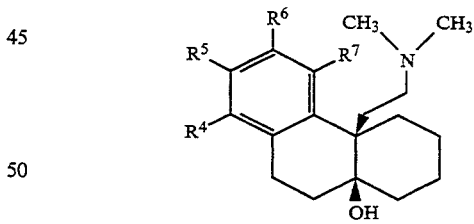

wherein all of the groups $R^4$, and $R^5$, $R^6$ and $R^7$ are hydrogen, or three of the groups $R^4$, $R^5$, $R^6$ and $R^7$ are hydrogen and the remaining group is halogen or hydroxy.

12. The compound of claim 11 wherein $R^4$, $R^5$, and $R^7$ are hydrogen and $R^6$ is halogen or hydroxy.

13. The compound of claim 11 wherein said compound is rac-cis-4b-(2-Dimethylamino-ethyl)-4b,5,6,7,8,8a,9,10-octahydro-phenanthren-8a-ol.

14. The compound of claim 12 wherein said compound is rac-cis-3-Chloro-4b-(2-dimethylamino-ethyl)-4b,5,6,7,8,8a,9,10-octahydro-phenanthren-8a-ol.

15. The compound of claim 12 wherein said compound is (−)-cis-3-Chloro-4b-(2-dimethylamino-ethyl)-4b,5,6,7,8,8a,9,10-octahydro-phenanthren-8a-ol.

16. The compound of claim 12 wherein said compound is (+)-cis-3-Chloro-4b-(2-dimethylamino-ethyl)-4b,5,6,7,8,8a,9,10-octahydro-phenanthren-8a-ol.

17. The compound of claim 12 wherein said compound is rac-cis-4b-(2-Dimethylamino-ethyl)-4b,5,6,7,8,8a,9,10-octahydro-phenanthrene-3,8a-diol.

18. The compound of claim 12 wherein said compound is rac-cis-4b-(2-dimethylamino-ethyl)-3-fluoro-4b,5,6,7,8,8a,9,10-octahydro-phenanthren-8a-ol.

19. The compound of claim 3 having the formula:

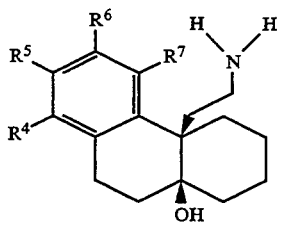

wherein three of the groups $R^4$, $R^5$, $R^6$ and $R^7$ are hydrogen and the remaining group is halogen or hydroxy.

20. The compound of claim 19 wherein the groups $R^4$, $R^5$, and $R^7$ are hydrogen and the group $R^6$ is halogen or hydroxy.

21. The compound of claim 20 wherein said compound is rac-cis-4b-(2-Amino-ethyl)-3-fluoro-4b,5,6,7,8,8a,9,10-octahydro-phenanthren-8a-ol.

22. The compound of claim 20 wherein said compound is rac-cis-4b-(2-amino-ethyl)-3-chloro-4b,5,6,7,8,8a,9,10-octahydro-phenanthren-8a-ol.

23. The compound of claim 20 wherein said compound is rac-cis-4b-(2-amino-ethyl)-3-bromo-4b,5,6,7,8,8a,9,10-octahydro-phenanthren-8a-ol.

24. The compound of claim 20 wherein said compound is rac-cis-4b-(2-amino-ethyl)-4b,5,6,7,8,8a,9,10-octahydro-phenanthrene-3,8a-diol.

25. The compound of claim 20 wherein said compound is (+)-cis-4b-(2-amino-ethyl)-4b,5,6,7,8,8a,9,10-octahydro-phenanthrene-3,8a-diol.

26. The compound of claim 20 wherein said compound is (−)-cis-4b-(2-amino-ethyl)-4b,5,6,7,8,8a,9,10-octahydro-phenanthrene-3,8a-diol.

27. A method for the prevention of neuronal damage due to hypoxia or ischemia in a host which comprises administering to the host an effective amount of a compound wherein the compound is rac-cis-4b-(2-amino-ethyl)-4b,5,6,7,8,8a,9,10-octahydro-phenanthrene-8a-ol or a pharmaceutically acceptable acid addition salt thereof.

28. The method of claim 27 wherein the compound is administered orally and the amount is from 50–500 mg per day.

29. A pharmaceutical composition for the prevention of neuronal damage due to hypoxia or ischemia in a host which comprises an effective amount of rac-cis-4b-(2-amino-ethyl)-4b,5,6,7,8,8a,9,10-octahydro-phenanthren-8a-ol or a pharmaceutically acceptable acid addition salt thereof and a pharmaceutically acceptable excipient.

* * * * *